(12) United States Patent
Howard

(10) Patent No.: US 11,957,431 B2
(45) Date of Patent: Apr. 16, 2024

(54) ANTI-PATHOGENIC SYSTEM

(71) Applicant: Fredrick Todd Howard, Banning, CA (US)

(72) Inventor: Fredrick Todd Howard, Banning, CA (US)

(73) Assignee: AIR FORCE-FIELD SYSTEMS LLC, Chino Hills, CA (US)

( * ) Notice: Subject to any disclaimer, the term of this patent is extended or adjusted under 35 U.S.C. 154(b) by 0 days.

(21) Appl. No.: 18/031,230

(22) PCT Filed: Oct. 11, 2021

(86) PCT No.: PCT/US2021/054453
§ 371 (c)(1),
(2) Date: Apr. 11, 2023

(87) PCT Pub. No.: WO2022/081496
PCT Pub. Date: Apr. 21, 2022

(65) Prior Publication Data
US 2023/0392806 A1 Dec. 7, 2023

Related U.S. Application Data

(60) Provisional application No. 63/090,285, filed on Oct. 12, 2020, provisional application No. 63/122,474, filed on Dec. 8, 2020, provisional application No. 63/176,369, filed on May 6, 2021, provisional application No. 63/194,890, filed on May 28, 2021.

(51) Int. Cl.
*A61B 5/00* (2006.01)
*A41D 13/11* (2006.01)
*F24F 7/003* (2021.01)
*F24F 8/30* (2021.01)
*F24F 9/00* (2006.01)
*G16H 40/63* (2018.01)
*G16H 40/67* (2018.01)

(52) U.S. Cl.
CPC ........ *A61B 5/0002* (2013.01); *A41D 13/1184* (2013.01); *F24F 7/003* (2021.01); *F24F 8/30* (2021.01); *F24F 9/00* (2013.01); *G16H 40/63* (2018.01); *G16H 40/67* (2018.01)

(58) Field of Classification Search
CPC ..... F24F 9/00; F24F 8/30; F24F 7/003; A41D 13/1184
USPC ........................................................ 454/188
See application file for complete search history.

(56) References Cited

U.S. PATENT DOCUMENTS 3,726,203 A * 4/1973 Lindestrom ............ A61G 10/02
55/467
4,054,084 A * 10/1977 Palmer ...................... F24F 9/00
169/61

(Continued)

*Primary Examiner* — Avinash A Savani
*Assistant Examiner* — Dana K Tighe
(74) *Attorney, Agent, or Firm* — Chad Peterson

(57) ABSTRACT

The disclosed system comprises a primary air curtain system and one or more optional apparel and/or accessory air curtain subsystem components. The primary system and subsystem(s) are configured to create a directionally controlled air curtain effect that repulses, repels, redirects, neutralizes, and/or disperses airborne infectious pathogens, carcinogens, chemicals, and other contaminants away from the body of a user or a surface susceptible to foreign contamination within a protected enclosure.

49 Claims, 11 Drawing Sheets

(56) References Cited

U.S. PATENT DOCUMENTS

| | | | | |
|---|---|---|---|---|
| 4,964,282 | A * | 10/1990 | Wagner | B62J 33/00 |
| | | | | 2/DIG. 1 |
| 5,046,492 | A | 9/1991 | Stackhouse et al. | |
| 7,036,502 | B2 * | 5/2006 | Manne | A62B 18/003 |
| | | | | 128/200.27 |
| 8,057,380 | B2 * | 11/2011 | Kuo | A61G 11/00 |
| | | | | 237/3 |
| 8,479,727 | B2 * | 7/2013 | Grove | A62B 18/006 |
| | | | | 128/201.25 |
| 9,057,528 | B2 * | 6/2015 | Browne | B60J 10/242 |
| 10,314,989 | B2 * | 6/2019 | Goff | A61B 5/6803 |
| 10,448,685 | B2 * | 10/2019 | Czajka | A41D 13/1218 |
| 10,449,844 | B2 * | 10/2019 | Le Bastard | B61D 19/02 |
| 10,962,246 | B2 * | 3/2021 | Bromley | F24F 9/00 |
| 11,649,976 | B1 * | 5/2023 | Galvin | F24F 3/163 |
| | | | | 454/75 |
| 2005/0282485 | A1 * | 12/2005 | Kato | B60H 1/243 |
| | | | | 454/136 |
| 2012/0111190 | A1 | 5/2012 | Dariavach et al. | |
| 2017/0372216 | A1 | 12/2017 | Awiszus et al. | |
| 2019/0226702 | A1 | 7/2019 | Nolan et al. | |
| 2021/0239336 | A1 * | 8/2021 | Edwards | F24F 5/0042 |

\* cited by examiner

ANTI-PATHOGENIC SYSTEM

CROSS-REFERENCE TO RELATED APPLICATIONS

The present application claims the benefit of U.S. Provisional Application No. 63/194,890, entitled "Anti-Contaminate Primary System Enclosure and Apparel Garment and Accessory Subsystem Extension," filed May 28, 2021; U.S. Provisional Application No. 63/176,369, entitled "Anti-Contaminate Primary System Enclosure and Apparel Garment and Accessory Subsystem Extension," filed May 6, 2021; U.S. Provisional Application No. 63/122,474, entitled "Anti-Contaminate Air Force-Field Enclosure And Body Worn Mobile Subsystem Facilitator," filed Dec. 8, 2020; and U.S. Provisional Application No. 63/090,285, entitled "Anti-Contaminate Work Station Primary System and Utility Apparel Accessory Body Subsystem," filed Oct. 12, 2020, the contents of which are hereby incorporated by reference herein in their entireties.

TECHNICAL FIELD

The present disclosure is relates to air curtain enclosures and air curtain apparel, garment, and accessory extensions.

BACKGROUND

The Covid-19 pandemic has reinforced the continued need for anti-contaminant devices and maintainable sterile environments in buildings and work spaces. Anti-contaminant devices are used to protect from various types of contaminants, such as smoke, allergens, pollen, dust, spores, toxic chemicals, undesirable odors, insects (e.g., gnats and mosquitoes), airborne pathogens (e.g., viruses that cause Covid-19, common colds, influenza, SARS, ebola, tuberculosis, etc.), etc.

The first known record of an air curtain was in 1904. Although the terms may be used synonymously, in North America "air door" is more often referred to as an "air curtain." Air curtains and air doors function differently from the present system.

Webster defines an air curtain as: an artificially created stream of air that is blown across a doorway or other opening to create a barrier (as for repelling insects or preventing heat transfer). The American Society of Heating, Refrigerating and Air-Conditioning Engineers (ASHRAE) defines air-curtains as follows: "In its simplest application an air curtain is a continuous broad stream of air circulated across a doorway of a conditioned space. It reduces penetration of insects and unconditioned air into a conditioned space by forcing an air stream across the entire entrance. The airstream moves with velocity and angle such that any air that tries to penetrate the curtain is entrained. Air curtain effectiveness in preventing infiltration through an entrance generally ranges from 60 to 80%."

In 1888 Theophilus Van Kannel received a patent (U.S. Pat. No. 387,571) on the first air-door, also known as the revolving door. The purpose of Kannel's invention was to prevent cold air from the outside of a building from moving inside, and to also greatly reduce noise pollution.

Kannel's system circulated air in a clockwise or counterclockwise direction but was not designed for launching air mass away from person's body or respiratory system.

Additionally, Kannel's system wasn't designed to protect individuals within a command control, utility, or leisure area with wearable subsystem components of the parent system extending protection to individuals beyond the protective area.

Anti-contaminant and maintainable sterile environment dwellings and work spaces are the very foundation of human survival in everyday life and are as necessary as food and water to ensure survival from the elements. Some of these elements include: acidic rain, heat cold, cacogenic smoke, foul odors, allergens diseases, etc., as well as airborne pathogens that can also be transported by flying insects such as disease-carrying mosquitoes, flies, gnats, etc.

For example, even as far back as the pre-historic era, early men and women would shield themselves within various structures or formations from the elements by making their dwellings, work, and leisure areas, however crude, as environmentally breathable and habitable as possible. To escape the elements man would often construct their homes and work areas from fortifications such as caves, tents, cabins, tree houses, and eventually modern homes, expansive apartments and condominiums and large office buildings and skyscrapers.

And so, when ancient (and modern) men and women ventured from their obsolete dwellings and places of work, they found they were in needed of anti-contaminant extensions of protection from the semi-protective environments in which they had worked or live, and which had afforded them centuries of protection. Some of these past and current contaminant-resistant extensions found in their homes, dwellings, or places of work have included sleep coverings, clothing apparel, and wearable accessories and garments to cover up their arms, hands, legs, and necks, as well as manual and electric lightweight material hand fans to disperse smoke, allergens, toxic odors, heat, swarming gnats, and mosquitos as well as body-wearable accessories to cover the eyes and mouth such as masks, scarves, eyeglasses, goggles, face shields, hats, boots, etc.

In additional to the aforementioned, men and women have gone to great lengths to ensure that their homes and work station environments are as disease free and environmentally safe as possible from over exposure to harmful airborne pathogens, chemicals, and carcinogens including natural and man-made substances such as: the Covid-19 virus (coronavirus), influenza viruses, cold viruses, aerosols, chemicals, pollen, smoke, toxic steam, disease-carrying insects, etc.

For example, sterile work environments may include medical treatment centers, operating rooms, scientific research facilities, as well as chemical plants and business transaction counter and work stations where employees are exposed to both long- and short-term hazardous chemicals, airborne germs, and/or smoke.

These work stations may also take the form of transportable and/or convertible tactical public safety mobile or ICS (Incident Command) headquarters vehicles such as crime scene investigation trailers, buses, patrol vehicles, SWAT vehicles, or other initial-response police and/or logistical law enforcement support-related vehicles.

Additionally, large-scale mobile anti-contaminant ICS vehicles include forestry fighter trucks and rescue vehicles as well as urban fire truck and rescue ladder bucket vehicles, which may also be designated as initial-response short- or long-term command-and-control or incident command headquarter vehicles.

The air quality environments within these stationary and mobile command and control enclosures are often mandated by local, state, and/or federal laws and regulatory boards or commissions such as the EPA and OSHA as well as state and county departments of health and safety established to ensure environmentally-safe compliance with mandates to prevent mass population infections and contamination outbreaks.

Known air curtains primarily focus on protecting a doorway or barrier opening into a building or structure and disclose only slight innovations of the original purposes (i.e., protecting an entrance or exit).

The prior art does not teach a supplemental family of personnel protective equipment (PPE) extensions on a person, animal, or other living organism (e.g., a plant) beyond a contained command and control, work, utility, experimental, or leisure area via the application of body-worn apparel, garments, or accessory subcomponents in communication with a parent enclosure, to signal a decontamination event upon egress or ingress beyond or within the protective enclosure. Neither does the prior art teach that such extensions may be operated independently of the parent (or primary) system.

The art also fails to teach the aforementioned process, whereby the protective extensions are predicated upon an individual donning or attaching a wearable air curtain system device that pushes exported mass matter away from at least one direction of a person's body, nor does the prior art disclose that the wearable protective extensions may be integrated with a motion detection means such as an accelerometer.

One slight variation beyond the traditional air curtain is Xiaofeng (Chinese Pat. CN2122530055U). Xiaofeng teaches an air curtain machine that produces ozone, comprising a rack, fan, and a control device, wherein a cavity is formed within the rack. The rack is provided with an air inlet and an air outlet. An ozone generator is placed within the cavity for outputting ozone gas, thus disinfecting people as they pass through the air curtain.

Xiaofeng does not teach a wearable hardware system solution protective parent enclosure or subsystem extension. The method of deployment is unremarkable, in that Xiaofeng merely teaches the practicality of traditional air curtains but from the perspective of disinfection. Additionally, significant exposure to ozone generators has been shown to cause serious negative effects on a person's respiratory system and overall health without adequate filtration.

Xiaofeng also fails to teach a protective enclosure optionally expelling an air curtain from at least one to a plurality of directions away from a protective area or a person's body who is wearing at least one subcomponent of the parent systems around or attached to the person's body, nor does Xiaofeng cite using any wearable subcomponents as extensions beyond the protective area for the purpose of preventing cross contamination and activating a warning system upon reentering a protective area should a communication algorithm linking the systems be disrupted.

Additionally, because Xiaofeng is based on the traditional air curtain model, with the exception of employing a rack and cavity system for generating ozone, Xiaofeng also fails to disclose that its area of protection can also be an enclosure within a motor-driven or mobile command and control, work, utility, experimental, or leisure area. As such, the functionality of Xiaofeng is unrelated in scope to the purpose and intent of the proposed system.

Korean Pat. KR20010022820A relates to a system for face and respiratory protection. Unlike the present system, KR20010022820A proposes a system primarily designed for medical settings by applying a method of comfort and ease of use for the wearer while donning the system.

KR20010022820A proposes a face protection system wherein the face protector and the wearer's face substantially form a breathing area within the mask. A bag-shaped filter surrounds the outside of the blower and provides filtered air to the breathing area, and the exhaust filter is coupled with a face guard.

KR20010022820A cites the benefit of protecting the user from contamination while also protecting the environment (including non-wearers) from the user to include protecting patients. Additionally, KR20010022820A describes a face mask and shield system which form fits around the face and is anchored to the top portion of the head for increased stability without the necessity of traditional straps around the head.

While perhaps a solution in terms of comfort and to mutually safeguard anti-contaminant environments for individuals and professionals, (i.e., doctors and patients), KR20010022820A does not teach a wearable hardware system solution protective parent enclosure or subsystem extension to prevent, deter, or reduce the negative effects of contaminants, airborne carcinogens, pathogens, and allergens.

KR20010022820A also fails to teach a protective enclosure expelling an air curtain from at least one to a plurality of directions away from a protective area or a person's body who is wearing at least one subcomponent of the parent system around or attached to the person's body, nor does KR20010022820A cite using any wearable subcomponents as extensions beyond the protective area for preventing cross contamination upon reentering the protective area.

Unlike KR20010022820A, the present system is designed to protect a person in the course of performing his/her duties from contaminated environments such as battlefield operating rooms, forestry fire mobile and stationary command centers, or law enforcement ICM staging areas where gases or smoke may be deployed, etc. Neither KR20010022820A nor Xiaofeng protect the environment or person(s) outside of the protective enclosure.

The disclosed system offers several very different solutions from KR20010022820A and Xiaofeng, e.g., that it deploys a curtain of air directly away from a person while within an enclosure. It then extends the protective air curtain beyond the enclosure by equipping an individual with apparel and apparel attachments, garments and garment attachments, and accessories and accessory attachments that communicate with the parent system to alert or warn the wearer to prevent or reduce occurrences and epidemics of cross and mass contamination. Neither KR20010022820A nor Xiaofeng disclose such a system.

Russell (U.S. Pat. No. 7,077,137B2) introduces as a system for filtering, diffusing, and conditioning inhaled air. The device is attached to an eyewear system for convenience of use and includes air permeable membranes surrounding the nose for normal breathing and is easily removed and suitable for daily use. Russell describes a method of convenience relating to delivering filtered air into an individual's respiratory system via an eyewear system attachment. However, the proposed system, more specifically the eyewear subsystem, delivers a force field curtain of air mass forward or away from the body, which is not disclosed in Russell.

Decontamination chambers are also known in the art and are generally predicated upon the sterilization of articles such as medical supplies and personnel working in high contaminant environments subject to exposure. These areas may include places such as chemical factories as well as biological and nuclear testing and experimentation facilities.

These chambers work along similar design principles, primarily involving the following steps:

A. The person removes a piece of equipment or clothing from a sterile environment.
B. The person or equipment is donned or prepared outside of the sterile environment but usually in a safe environment.
C. The person or equipment is introduced into a non-sterile or contaminated environment to complete a task or serve a purpose.
D. The person or equipment is removed from the non-sterile or contaminated environment and the environment is evacuated of the contaminants to the greatest extent possible.
E. If the person or equipment is removed from the environment the person or equipment is introduced into a chamber or wash setting and the chamber is secured.
F. A decontamination agent is introduced into the setting and the person or equipment is decontaminated or sterilized by various means practiced in the art.
G. The person or equipment is returned to a sterile environment to the extent possible or to an environment free of the harmful agents.

Wiget (WO 2014165428A) introduces a transportable vacuum assisted decontamination unit comprising a housing which contains a decontamination chamber and a decontamination processing section, and a master pallet on which the housing is positioned. Wiget's system also has at least one gas inlet and at least one gas outlet for importing and evacuating gaseous decontaminant agents.

However, none of what Wiget proposes indicates a primary system whereby the system exports mass matter away from an occupied enclosure nor does Wiget mention any integration with any subsystem components of the parent system in communication with a least one of the subsystem components to introduce a decontamination alert system.

Johnson (U.S. Ser. No. 10/577,744B2) teaches a fabric with a contaminant resistant nanoparticle coating that is applied during the fabrication process. Unlike the present invention, Johnson does not teach an air curtain system or device that utilizes exported air or other mass matter to repel airborne contaminates away from a wearer.

Additionally, Johnson fails to teach a system wherein clothing, apparel, garments, and/or accessories are integrated with a primary system or device and are in communication with the primary system to alert of a decontamination event.

Shankman (U.S. Pat. No. 4,858,256A) teaches a chemical equipment decontamination truck for man-carried equipment washing down personnel at a major chemical disaster. The vehicle contains equipment for decontaminating the equipment used by emergency personnel so that the man-carried equipment can be brought back into service quickly. Additionally, Shankman proposes that contaminated liquids are retained in the truck for disposition or are decontaminated before being returned to the environment.

Shankman also discloses a transportation means, specifically a truck, that is compartmentalized for various processes of decontamination. However, none of Shankman's aforementioned processes would suggest to one of ordinary skill in the art a vehicle as a protective enclosure expelling an air curtain from at least one to a plurality of directions away from the truck or a protective area or a person's body who is wearing at least one subcomponent of the parent systems around or attached to the person's body, nor does Shankman cite using any wearable subcomponents as extensions beyond the protective area for the purpose of preventing cross contamination upon reentering the truck vehicle.

Shankman's invention also fails to propose a mobile command-and-control system or method to import or export any mass or volume substance away from its enclosure or perimeter to protect personnel who are contained inside.

Therefore, Shankman's disclosure is fundamentally different from the present system, because Shankman's objective is to contain and decontaminate personnel and items within its enclosure while a purpose of disclosed system is to expel airborne decontaminants away from an enclosure or person.

There is currently a need in the art for a more flexible and protective anti-contaminant system, that includes an anti-contaminant protective enclosure and one or more subsystem extensions to prevent, deter, or reduce contaminants, e.g., carcinogens, pathogen, and/or allergens.

SUMMARY

In accordance with the foregoing objectives and others, exemplary methods and systems are disclosed herein to provide an anti-contaminant system. The disclosed methods and systems provide an anti-contaminant and anti-pathogenic air-force-field curtain barrier designed for work utility protection, fire and EMS protection, fire response and rescue (e.g., structure, forestry, etc.) protection, law enforcement and public safety protection, infant protection, as well as for anti-contaminant medical and respiratory pediatric and geriatric preventive care treatment. The system may also assist in preventing airborne contaminants and pathogenic carrying insects from contacting immune deficient patients on respirators or other life support systems in medical environments.

In general, the disclosed system comprises a primary air curtain system that protects a protected area, and one or more apparel and/or accessory air curtain subsystem components that are worn by people who are inside or in proximity to the protected area. The primary system and subsystem(s) are configured to create one or more directionally controlled air curtain effects that repulse, repel, redirect, neutralize, and/or disperse airborne infectious pathogens, carcinogens, chemicals, and other contaminants away from the body of subsystem users or a surface susceptible to contamination within a protected enclosure.

The primary system may comprise one or more devices that expel mass, such as air or water, from within the protected area. The protected area may be a work, command, or leisure enclosure; a specialized sterile environment (such as a manufacturing facility); a classroom; a mobile command platform (e.g., firetruck); or any other area from which there is a need to remove contaminants.

The primary system and the subsystem(s) may act together or independently of each other, and may be linked by communication methods known in the prior art. In an embodiment, the communication (or lack thereof) between the primary system and the subsystem(s) may signal the need for a decontamination event.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Figure 1:
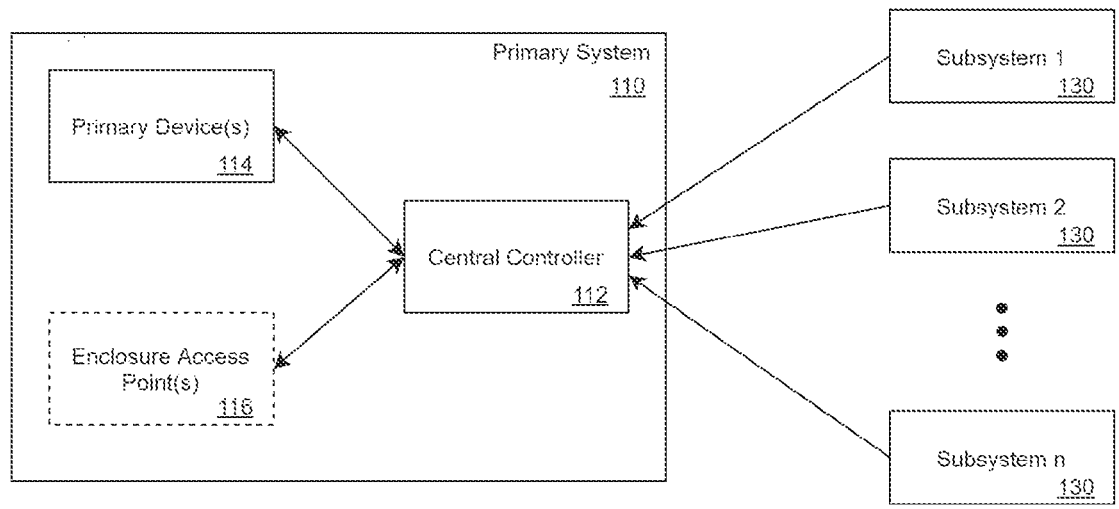
FIG. 1 illustrates an embodiment of a system according to an aspect of the present invention.

Referring now to FIG. 1, an embodiment of the overall anti-contaminant system comprises a primary system 110 and one or more apparel and/or accessory subsystems 120 that work together to protect the occupants of and/or personnel accessing a sterile, protected, and/or hazardous area. The primary system and subsystems disperse contaminants, including pathogens, away from the protected area occupied by living organisms susceptible to infection and/or contamination.

The overall system is multi-tiered and integrates apparel, garments, apparel attachments such as straps, pockets, hooks, belts loops, ties, clips, etc., and/or accessories such as eyewear, face masks, forearm guards, leg guards, belts, gloves, etc., to deliver a protective air curtain projected outward from the user's body, and particularly away from the user's eyes, skin, nose, and mouth.

The system provides protection to users both inside and outside the protected enclosure. Protection inside the enclosure is primarily provided by the primary system 110. Protection outside the enclosure is provided by the worn subsystems 120. The primary system and the subsystem(s) on users' apparel, garments, accessories, etc., are in communication (e.g., via internet, WAN, LAN, WLAN, cellular signals, etc.) so that the primary system can monitor the status and location of the subsystem(s).

The primary system includes a central controller 112, one or more primary devices 114, and one or more optional enclosure access points 116. The central controller 112 comprises one or more computing devices, and is in communication with the primary devices 114, optional enclosure access points 116, and the subsystems 120.

The primary devices 114 comprise one or more mass projection means including fans, turbine systems, pressure release systems, negative and positive currents, etc. The system uses the mass projection means 114 to separate at least one defined area or radius (e.g., the protected enclosure) from another defined area by introducing a mass barrier (such as exported air) to prevent intrusion into the protected area from foreign contaminants, thereby preventing or reducing cross contaminations and infections.

Optional enclosure access points 116 comprise an entry and/or exit device, e.g., a door. The access points are in communication with the central controller 112, such that the central controller 112 may deny entrance to a user that needs to be decontaminated by, e.g., preventing the door from opening.

The mass projection means may be affixed at or integrated within at least one single access point proximate to at least one protective area, and up to 360 degrees vertically and/or horizontally around the top, bottom, sides, or floor of the protective enclosure.

The mass intake mechanism of the primary devices may be affixed to or integrated with an environmentally supplied mass source (e.g., may intake air from the environment) or the system may be self-contained employing an adjustable pressure source. The primary devices may also use one or more active and/or passive purification methods to kill, degrade, neutralize, and/or reduce dangerous or unhealthy airborne contaminants. Some of these purification methods include ionization currents, ozone generators, air purifiers, air filters, electrostatic filters, HEPA Filters, carbon activated filters, sprays, chemicals, UV lights, etc. The primary devices also optionally include a temperature and power output setting.

The mass projection means provide an air force field barrier which defends at least one to several people or living organisms within the protected area who would ordinarily be susceptible to airborne chemical contaminations or infectious dangers such as Covid-19, SARS, Ebola, tuberculosis, influenza, common colds, toxins, allergens, chemical aerosols, spoors, vapors, smoke, or steam. The force field barrier created by the system can also be used to repel germ and pathogen carrying insects such as flies and mosquitos from people, animals, and other living organisms within the protected area.

The primary system protected area may include various types of stationary or mobile platforms such as enclosed bank teller work or transaction barriers, construction trailers, forestry fire and EMS commands stations, incident command stations, heavy equipment enclosures where dust and harmful chemicals are released from building construction and demolition, hospitals and operating rooms, and law enforcement structures and holding facilities.

The subsystem components 120 may be attached to or integrated with at least one optionally worn piece of protective apparel or garments such as sweaters, jackets, vests, trousers, gloves, mittens, shirts, undergarments, etc., and/or at least one optional worn protective accessory devices such as eyewear, face masks, face shields, wristbands, watches, knee guards, shin guards, arm guards, elbow pads, hats, helmets, boots, etc. Each subsystem component comprises at least one expulsion device. The subsystem components are in communication with the primary system to alert the primary system when a decontamination event has occurred.

The primary and/or the subsystem(s) may intermittently or continually repulse, repel, deflect, diffuse, expel, neutralize, treat, and/or kill airborne contaminants encroaching within the protective area by directing forced, compressed, focused, expanded, flowing, sprayed, misted, liquefied, ionized, filtered, treated, cooled, and/or heated air or other mass matter away from at least one protective area.

In an embodiment, if a subsystem wearer tries to leave the enclosure without first activating any worn subsystems, the primary system can prevent the door from opening until the subsystems have been activated. Furthermore, if the primary system detects a situation where a user may potentially have been exposed to contaminants outside the enclosure (e.g., one of the user's subsystems was deactivated or communication between the subsystem and the primary system was disrupted), the primary system can prohibit the wearer's access to the enclosure until a decontamination process is completed.

To accomplish this, the system further comprises an optional alert that is triggered when the primary system and/or the subsystem(s) detect that either system failed to activate during any pendency period when the systems were apart or removed from the proximity of the other and then returned to the proximity of either system. The alert is for the purpose of initiating preventive decontamination (DECON) procedures prior to allowing re-entry into the protected area and establishing reintegration with the primary system.

Figure 2:
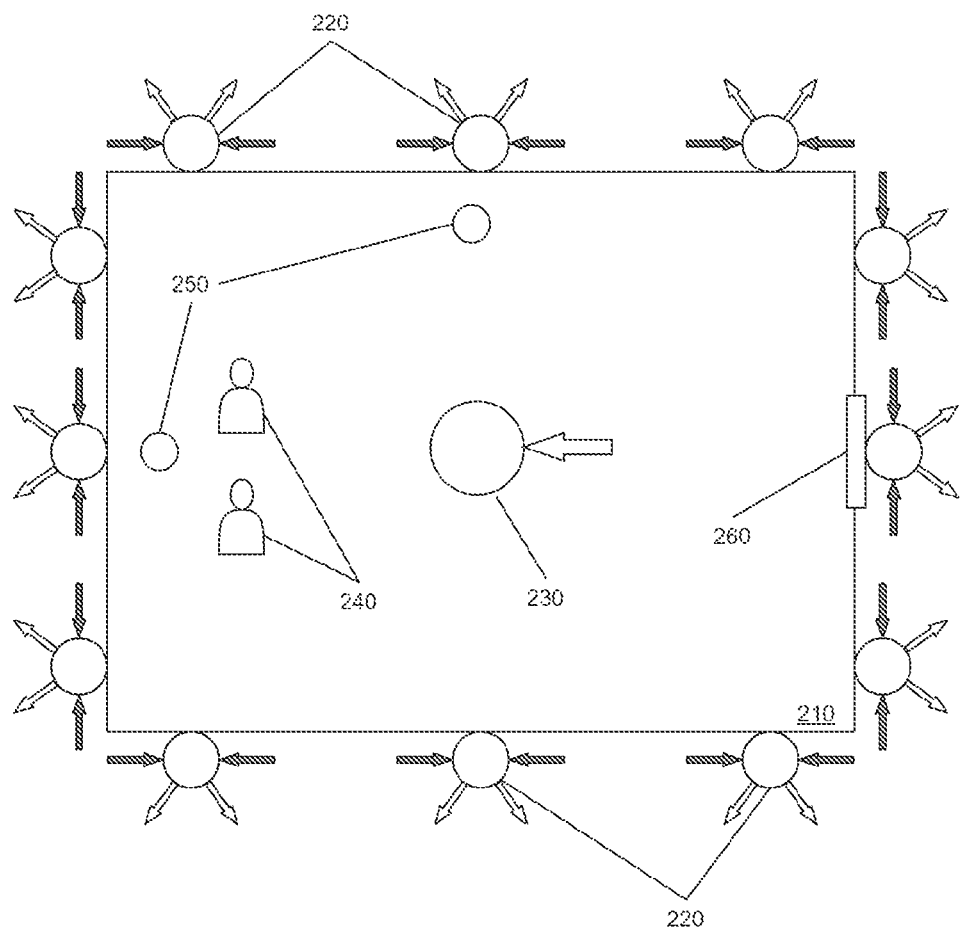
FIG. 2 illustrates an example primary system within a medical research facility.

FIG. 2 provides a top-down view of an example primary system 200 that is an enclosed work area within a medical research facility or experimentation laboratory that permits trained doctors and scientists to enter and exit hazardous areas within the facility at designated places and times. Within the facility may be a sterile area 210 enclosed by, e.g., steel walls and/or projectile resistant Plexiglas. The sterile area 210 may be accessed by one or more doors 260.

Several large (e.g., 3 meters×6 meters) anti-contaminant primary system devices 220 may line all sides of the enclosure. Each primary device is configured to import air from the environment (represented by the filled arrows) or a self-contained source (e.g., a compressed air source), optionally filter the mass, and export the mass to the environment (represented by the unfilled arrows). Because of the operation of primary devices, air continually flows away from the enclosure. Optionally, the primary devices may be vented to the enclosure. Primary devices are explained in more detail with respect to FIG. 3.

Disposed in the ceiling of the enclosure there may be one or more additional primary devices 230 that are configured to intake air and ionize or treat airborne contaminants that are vacuumed upwards (represented by the unfilled arrow) from the lower part of the enclosure. The primary devices 220 and ceiling primary devices 230 operate together to export contaminants from the protected enclosure. As such, personnel 240 working in the enclosure are protected from disease and harmful chemicals. In an embodiment, and as described further below, the personnel 240 may be wearing one or more subsystem devices to prevent cross-contamination when leaving and reentering the protected area. To keep a steady supply of oxygen for the personnel 240, one or more optional oxygen sources 250 may be provided within the enclosure.

Figure 3:
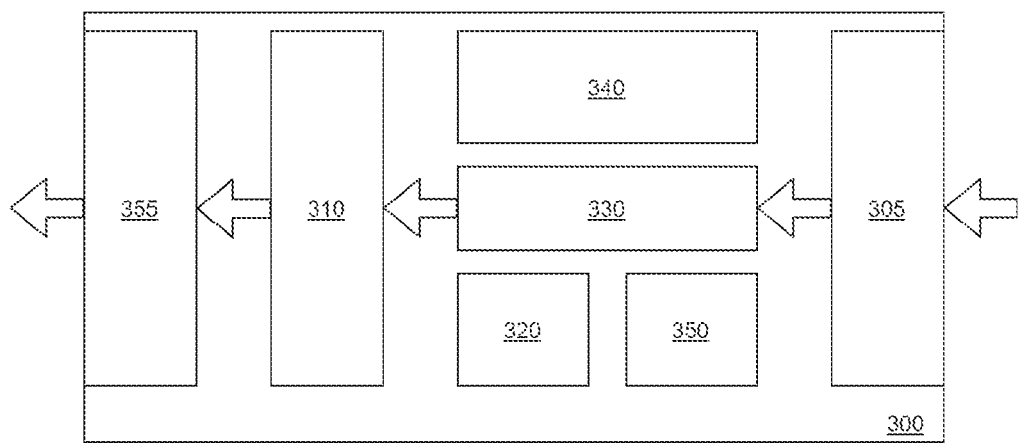
FIG. 3 illustrates an example primary system device.

FIG. 3 illustrates an example primary system device 300. As illustrated, each primary system device may comprise a mass intake port 305, mass expulsion means 310, a power source 320, a filtration system 330, a communication module 340, a control module 350, and a mass export port 355.

The mass expulsion means 310 may comprise any type of device for expulsion of mass, e.g., a fan driven by a motor, a blower, a pump, etc. The power source 320 may comprise any suitable source of power (e.g., a rechargeable or non-rechargeable battery) sufficient to power the mass expulsion means. When operating, the mass expulsion means intakes air (or other mass) through the mass intake port 305, passes it through the filtration system 330 to remove contaminants, and expels the air via mass export port 355, as shown by the large arrows.

The filtration system 330 may comprise one or more filtering devices, including, but not limited to, HEPA filters, carbon filters, electrostatic filters, ionizers, ozone generators, air purifiers, or any other applicable type of filter or combination thereof.

The control module 350 is configured to control the operation of the primary device, including the force produced by the mass expulsion means. For example, a fan may have an adjustable fan speed, and the fan speed may be user-adjustable or automatically adjusted based on environmental conditions. The control module is electrically connected to the mass expulsion means 310, the power source 320, the filtration system 330, and the communication module 340 to facilitate control of each module.

The communication module 340 is configured for electrical communication with one or more of: the central controller 112, other primary devices, and subsystem devices. The communication module may include a wired network interface, such as an Ethernet interface or a USB interface, or can include a wireless interface, such as an interface in compliance with an IEEE 802.xx standard, for example including Wi-Fi, Bluetooth, or WiMAX standards, or can include a combination thereof.

Returning to FIG. 2, the primary system devices may be fixed in placed around the periphery of the enclosure, or they may be mobile. The primary system devices may be synced together through operation of their communication modules 340, so they operate in unison to provide a constant pushing of air mass, and thereby airborne contaminants, away from the enclosure.

Personnel 240 coming into the sterile area may be required to wear hazardous material suits because the facility contains high concentrations of toxic chemicals or pathogens such as: cyanide, coronavirus, and/or various strains of influenza, which, if accidently released, could become airborne resulting in injury or death to people within and outside of the facility.

In an embodiment, the hazardous material suits may be equipped with one or more anti-pathogenic subsystem devices. For example, relatively large (e.g., 1 meter×1 meter) anti-pathogenic subsystem devices may be attached to strap and harness fixtures on the back of the PPE hazmat suits.

Additionally or alternative, the personnel may be wearing other protective devices, such as face shields, goggles, etc. In embodiments, a transparent face shield or pair of goggles may include one or more anti-pathogenic subsystem cylinders attached to or integrated into each side portion of the face shield or goggles.

Protocol within the facility may direct that upon entering or exiting an exposure area outside of the sterile area, a person who is wearing any anti-pathogenic (used synonymously with anti-contaminant) system device must have it continuously on upon entering, exiting, and reentering the controlled enclosure. This procedure may be applicable throughout the facility or to specific areas such as biological or chemical research and testing rooms depending on the potential exposure level to people, animals, and living organisms established by the governing or controlling authority.

Accordingly, the primary system devices and the subsystem devices (e.g., the anti-contaminant cylinders attached to or integrated into hazmat suits, goggles, face shields, etc.) are in communication with the primary central controller 112 that is configured to coordinate the operation of the primary system and subsystem devices.

The central controller 112 monitors the status, including location and operation status (e.g., on or off) of each primary system and subsystem device. The location of subsystem device(s) may be determined using any available location-determining means, e.g., GPS, proximity detectors, etc.

The central controller 112 may also be in communication with entry and exit doors of the sterile area and possibly throughout the facility, and can prevent a door from opening if the subsystem devices of the person requesting the door be opened are not operating.

In an alternative embodiment, each entry and exit door 260 may have a proximity detector that detects nearby subsystem devices, and the door may refuse to open if it detects a subsystem device nearby that is not turned on.

The system may require that the subsystem devices are on continually while outside the sterile area, or require the user to undergo decontamination before entering.

In designated areas the personnel anti-pathogenic subsystem devices may be turned off without causing a disruption in the communication algorithm of the system. However, if personnel attempt to enter a sterile or hazardous area without the worn subsystems being activated, the personnel will be denied entry, and may (depending on protocol) be required to undergo a decontamination procedure before being allowed into the sterile or hazardous area.

In an embodiment, animals, plants, or other living organisms within the controlled environment for experimentation purposes, may be secured in sterile portable carriers fitted with subsystem devices integrated within the enclosure's exposed openings, or secured on about or around the proximity of the enclosure's openings. The subsystem devices may be activated when manually transported from the controlled environment into other parts of the facility.

The subsystem expulsion device(s) can be incorporating into many different accessories, including, e.g., gloves, face masks, wristbands, forearm guards, eyeglasses, watches, etc. The expulsion device(s) may also be incorporated into work uniforms, medical uniforms, hazmat suits, or other items of clothing to additionally protect the wearer.

Primary system devices and subsystem devices may be configured to output a signal that indicates compatibility with the system, such as via a communication protocol, an application protocol, a SaaS application, a unique identifier, etc. This allows intercompatibility between components designed to be used with the system.

In an embodiment, the expulsion device(s) and/or the accessory and/or clothing incorporating the device may include a motion detector (e.g., an accelerometer). The subsystems may be configured such that triggering the motion detector activates the expulsion device(s), so users can quickly protect themselves, e.g., if someone nearby sneezes. The accelerometer (or other motion detector) will detect the sudden movement and cause the activation of the expulsion device. Alternative, a specific pre-determined movement (e.g., shaking the device two times in rapid succession) may trigger the expulsion device.

In an embodiment, the expulsion device(s) may be remotely controlled by an app on a suitable portable device (e.g., a cell phone, a tablet, etc.) that can detect the sound of someone sneezing nearby and automatically activate the expulsion device(s). The app may also be triggered by a particular motion, e.g., shaking the portable device two times in rapid succession.

Figure 4:
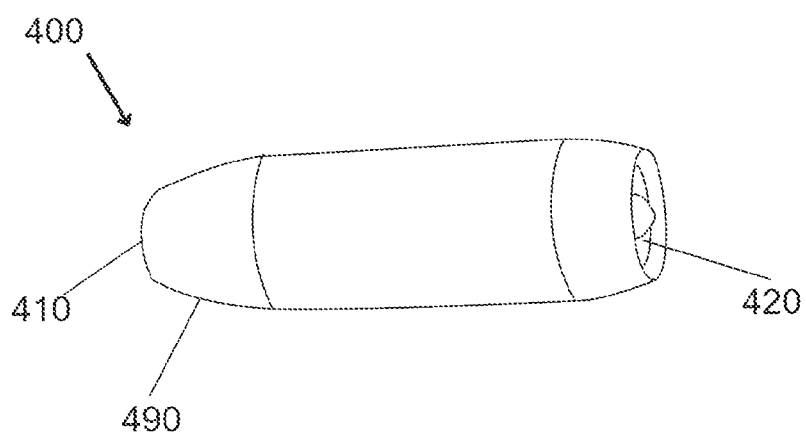
FIG. 4 illustrates an example subsystem device.
Figure 5:
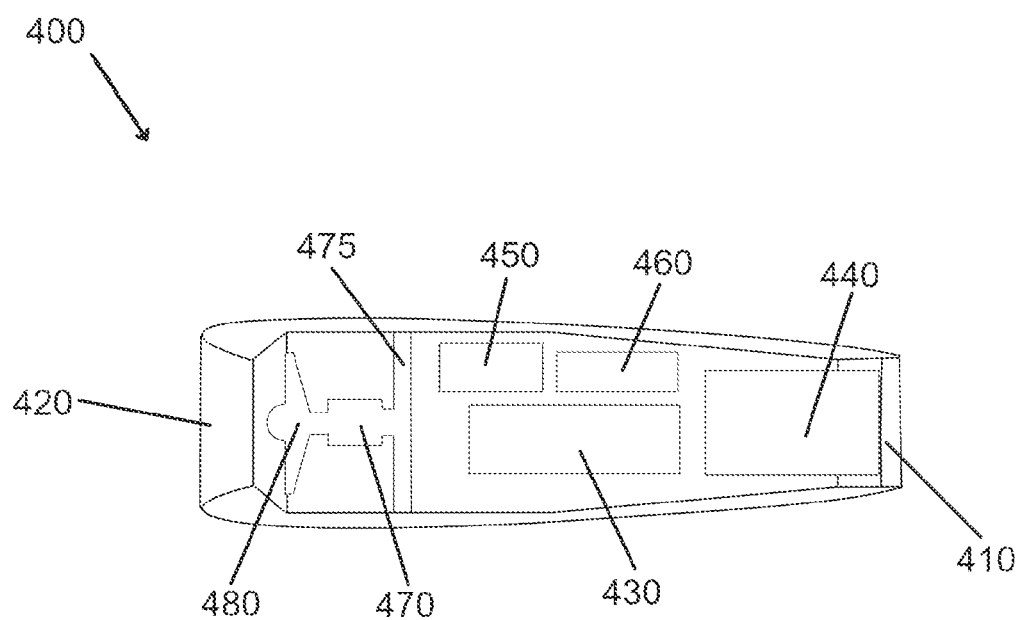
FIG. 5 illustrates a cutaway of an example subsystem device.

An embodiment of a subsystem expulsion device 400 is illustrated in FIGS. 4 and 5, in the form of a thrust cylinder. FIG. 5 is a cutaway view, showing the internal components of the thrust cylinder. Each thrust cylinder includes an intake opening 410, an export opening 420, a rechargeable battery 430, an ion generator 440, a fan speed controller 450, a communication module 460, a motor 470, a stator 475, and a fan 480. The thrust cylinder may also include several buttons (not shown), such as a power button, a fan speed button, and (optionally) an ionization button. Further, the thrust cylinder may include an internal filter, such as a HEPA filter and/or a carbon fiber filter (not shown) and a charging port (not shown) for charging the rechargeable battery 430.

The motor 470 may comprise a brushless, brushed, linear, servo, or stepper motor, and drives the fan 480 based on the fan speed set by the fan speed controller 450. The fan speed controller 450 may be user-controlled, e.g., via a fan speed button or switch. The ion generator 440 may be configured to generate negative ions when power is supplied, and may be controlled by a user-accessible switch or button.

The communication module 460 operates to electrically communicate with one or more of: the central controller 112, the primary devices, and other subsystem devices. The communication module may include a wired network interface, such as an Ethernet interface or a USB interface, or can include a wireless interface, such as an interface in compliance with an IEEE 802.xx standard, for example including Wi-Fi, Bluetooth, or WiMAX standards, or can include a combination thereof.

In an embodiment, the rechargeable battery may be accessed by twisting and removing one end, e.g., the intake end 490. The filter may also be replaceable by a similar process.

In operation, the motor 470 drives the fan 480, causing the intake opening 410 to import or take in air mass and contaminants, pass the air mass through the filter and ionizer 440 to remove contaminants, and expel the air through the export opening 420, thus thrusting or exporting air mass and contaminants away from a person or area.

If present, the ionization button may be configured to activate the ionizer 440, thus discharging negative particles into the air to eliminate airborne germs and contaminants. An additional option for the thrust cylinder is a button that activates a UV light that kills airborne pathogens.

In an embodiment, the export opening 420 may be adjustably focused (like a pair of binoculars) to push mass volume forward of the wearer's body to repel airborne contaminants at various distances. This adjustment would cause contaminant expulsion at narrower or wider demarcation points forward of or away from the wearer.

The thrust cylinders may be elongated or oval shaped, e.g., in a specific embodiment, they may be shaped like jet engines. They may be made of any suitable light-weight material, e.g., titanium, aluminum, steel, carbon fiber, etc.

In addition to their use for protection from contaminated air, thrust cylinders can be used for other purposes, such as cooling, clearing smoke, blowing away insects, etc. In an embodiment, a thrust cylinder may include an air-cooling element with user-adjustable temperature settings.

In an embodiment, instead of having an air intake opening, a thrust cylinder may be connected to a compressed air source that may be worn on the user's body, e.g., an air tank.

In an embodiment, a thrust cylinder may include an accelerometer or other device configured to detect motion. The accelerometer may be directly or indirectly electrically connected to the fan motor, so that when a sudden motion is made, the fan is activated. As such, the wearer of the thrust cylinder may quickly react to a contamination event (e.g., someone nearby sneezes) by quickly moving the subsystem device, and the fan will activate without the power button being pressed. In some embodiments, the motion that needs to be made may be user-selectable, e.g., a specific number of shakes, etc.

Figure 6:
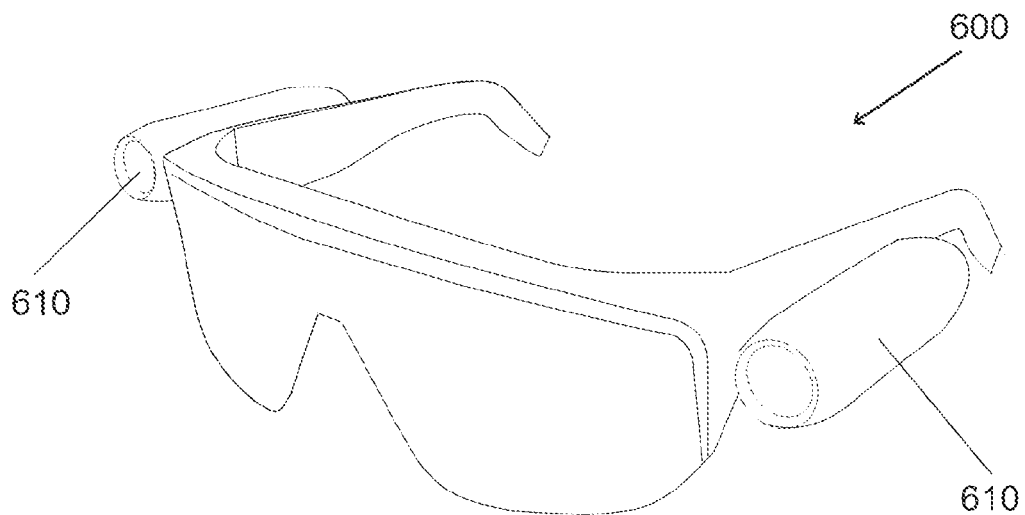
FIG. 6 illustrates an example of eyewear with attached subsystem devices.

In a particular embodiment illustrated in FIG. 6, a pair of eyeglasses 600 includes two detachable air mass thrust cylinders 610. Alternatively, the thrust cylinders may be integrated into the frames of the glasses. The thrust cylinders are positioned so that the export openings are forward of the lenses of the glasses, to prevent the exported air mass from interacting with the lenses, e.g., causing them to fog. Attachable thrust cylinders would include a receptacle that can snap onto or slide over eyeglass arms. In either embodiment, the air mass thrust cylinders may be rotatable to allow the user to alter or control the direction of the airflow.

Figure 7:
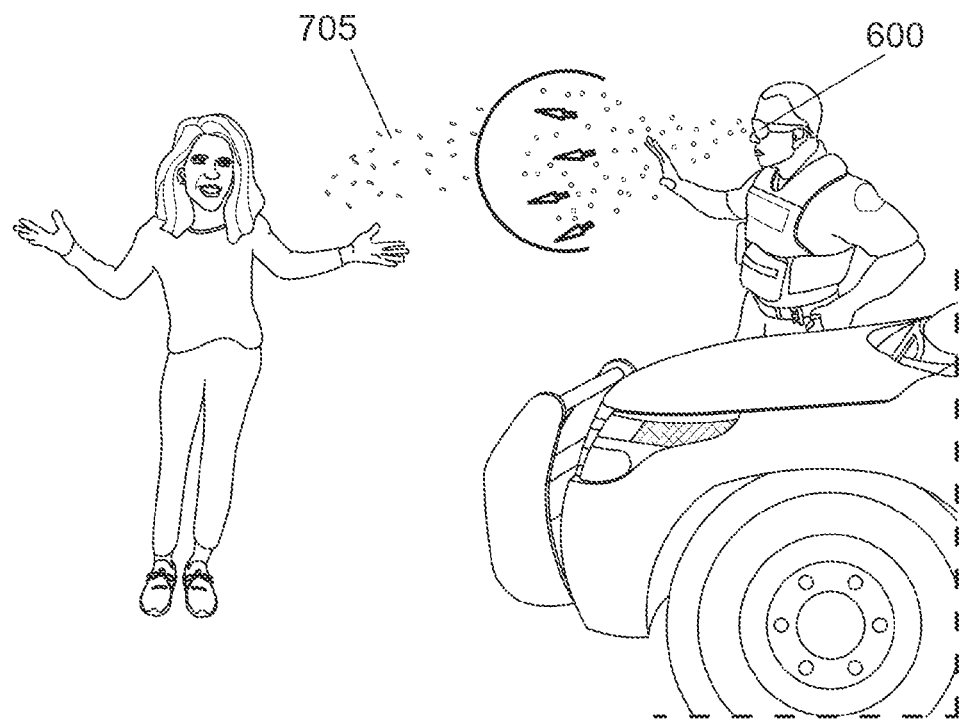
FIG. 7 illustrates an example of use of eyewear with attached subsystem devices.

FIG. 7 illustrates the eyeglasses 600 in use to protect a law enforcement officer from airborne pathogens 705 when interacting with a member of the public. When the officer activates the eyeglasses, the force of the expelled air (illustrated by arrows) pushes the airborne pathogens away, protecting the officer.

Thrust cylinders for use with eyewear may also include a filter screen placed over the intake opening to prevent foreign objects, e.g., bugs, hair, etc., from entering the cylinder.

In additional embodiments, thrust cylinders may be integrated into or attached to other facewear and face protection apparel, such as masks. On masks, the thrust cylinders may be attached proximate the jawline on either side, or a single cylinder may be attached under the chin.

In a particular mask embodiment, the mask may comprise multiple layers of material. Mass export devices may be configured such that, after importing, and optionally filtering and/or ionizing any imported contaminant, the air mass is then displaced throughout the periphery and between the bottom and top layered material of the mask where it is then exported though the outermost layer of the mask surface material via hundreds of small vent openings covering the front area of the mouth and nose cavity, as well as the entire multidirectional cross-section surface areas of the upper and lower jawline.

Mass export subsystems may also be integrated into a device that protects both the eyes and mouth, e.g., a firefighter mask. In this embodiment, mass can be projected from one or more vents and/or integrated with a mask attachment system (e.g., goggles, eye glasses, firemen's shield and mask systems, etc.). This pushes smoke and fire outwards and away from the firefighter's eyes, so he can see and rescue trapped people and animals in smoke- and fire-filled homes and structures. High pressure subsystem devices can also attached to the firefighter's clothing, or hung around his body, to push smoke and fire away.

With respect to the mask portion of a firefighter mask (e.g., the part that protects the mouth), one or more small mask export vents may be integral with or affixed to the surface area of the mask to force matter sideways over at least one cross-sectional surface area of the mask portion of the system.

This operates to form vertical and/or horizontal mass force-field barriers above the surface area of the mask and prevent airborne contaminants from contacting or adhering to the mask surface material to prevent cross contamination by a user's hands or other body parts on the material surface.

Figure 8:
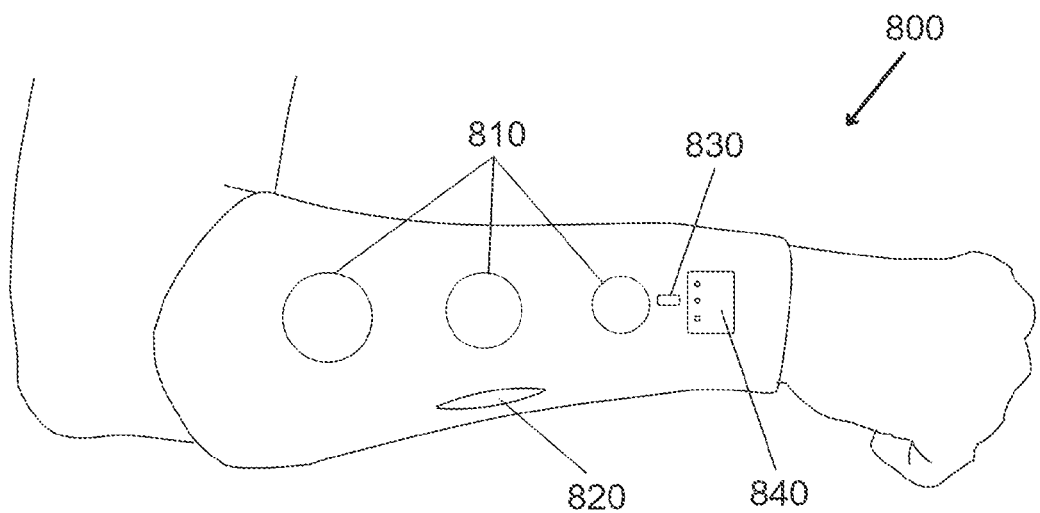
FIG. 8 illustrates an example of an armguard with integrated subsystem devices.

FIG. 8 illustrates an embodiment of an armguard 800 with one or more mass export vents 810. The armguard also includes an intake vent 820, a power button 830, and a display panel 840 including a fan speed button, an ionization button, and a sync button. One or more mass export devices, which function similarly as those described with respect to FIG. 4, are integrated within the armguard. The mass export devices intake air through the intake vent 820, filter the air with an internal filter and/or ionizer, and expel the filtered air out the export vents 810.

The buttons function as described with respect to FIG. 4. The sync button allows the armguard to sync with a portable device such as a cellphone (e.g., using Bluetooth). When synced with the armguard, the cellphone may be used to control settings of the armguard, e.g., through a downloadable cellphone app. Also, a setting may allow for motion of the cellphone (e.g., detected by an accelerometer) to signal the armguard device to activate. The display panel is configured to display the status of various settings, e.g., fan speed, etc., to the user.

Any of the other primary systems and/or subsystems disclosed herein may be synced with a cellphone (or other portable device) in like manner.

Figure 9:
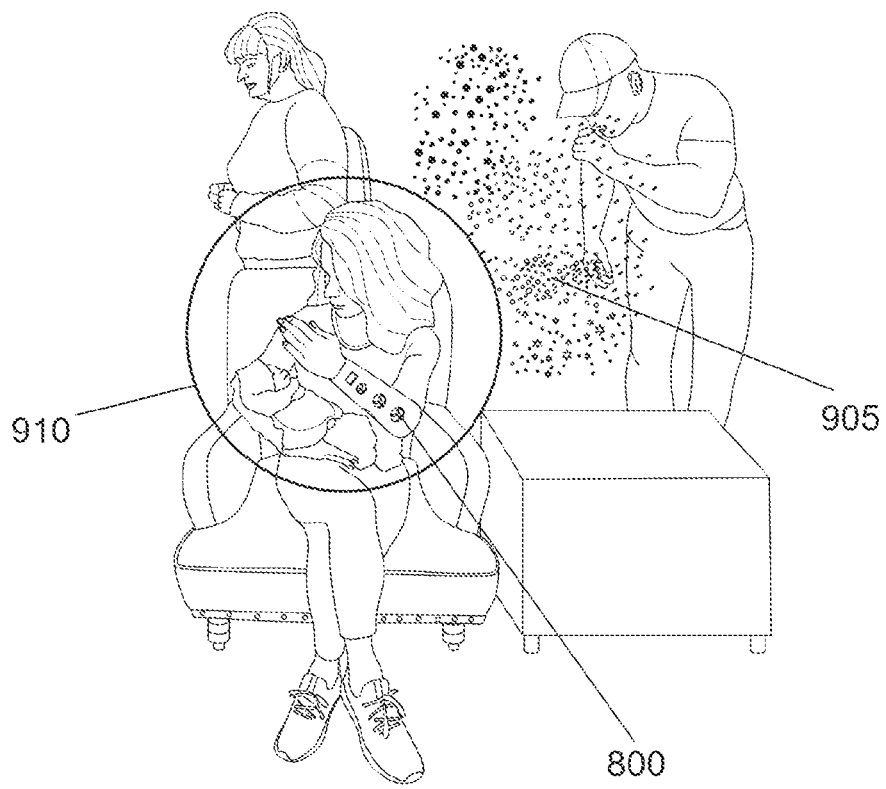
FIG. 9 illustrates an example of use of an armguard with integrated subsystem devices.

FIG. 9 illustrates the armguard 800 in use to protect an infant held by a caregiver. After a sneeze projects pathogens 905 into the air, the caregiver activates the mass export devices on the armguard. When the armguard's mass export feature is activated, the anti-contaminant function may be facilitated and enhanced by any combination of circular, waving, or cross-sectional motions of the wearer's arm over, about, or around the infant, thereby creating a multi-directional air force field shield 910 around the infant. As such, the manual motion by the wearer assists in pushing away airborne pathogens and contaminants descending down or projected towards an infant.

In another example, a glove may be equipped with a bracelet-like fitting that rotates around the circumference of the wrist. The wristband includes an enclosure snap-in anchor which is configured to receive a thrust cylinder.

The glove may be vented with a hollow hard material surface. The surface contours and follows the outside shape of the user's palm and allows the thrust cylinder(s) to align with a hollow plastic opening under the palm so that air mass that is exported from the device is channeled under the palm and out through the palm vents. This allows the user to open his or her hand wide and expel air mass from the palm area of the hand, causing filtered air mass to push smoke and irritants away from the user's body.

Figure 10:
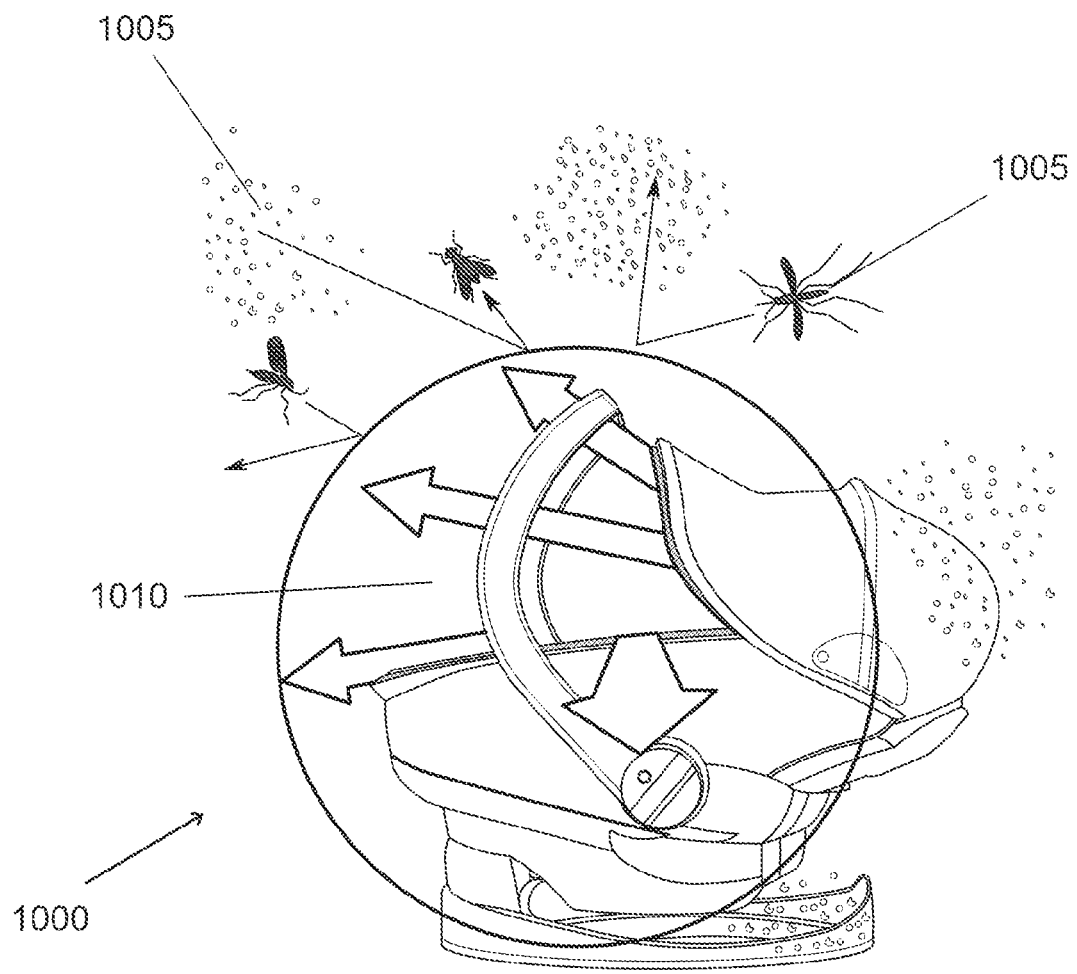
FIG. 10 illustrates an example of an infant carrier with integrated primary system devices.

Another embodiment, illustrated in FIGS. 10 through 13, uses multiple anti-pathogenic air-force-field system devices on an infant carrier 1000 to protect infants from disease. In a particular embodiment, several devices are positioned at strategic places around the infant carrier to blow away (as indicated by the arrows) pathogens and other contaminants 1005 as shown in FIG. 10. Infant carriers generally include at least one opening 1010 through which the infant may be retriever, and the devices may be place around the opening, e.g., proximate the periphery of the opening. In this embodiment, the devices primarily protect the opening of the infant carrier from pathogens and other contaminants.

Figure 11:
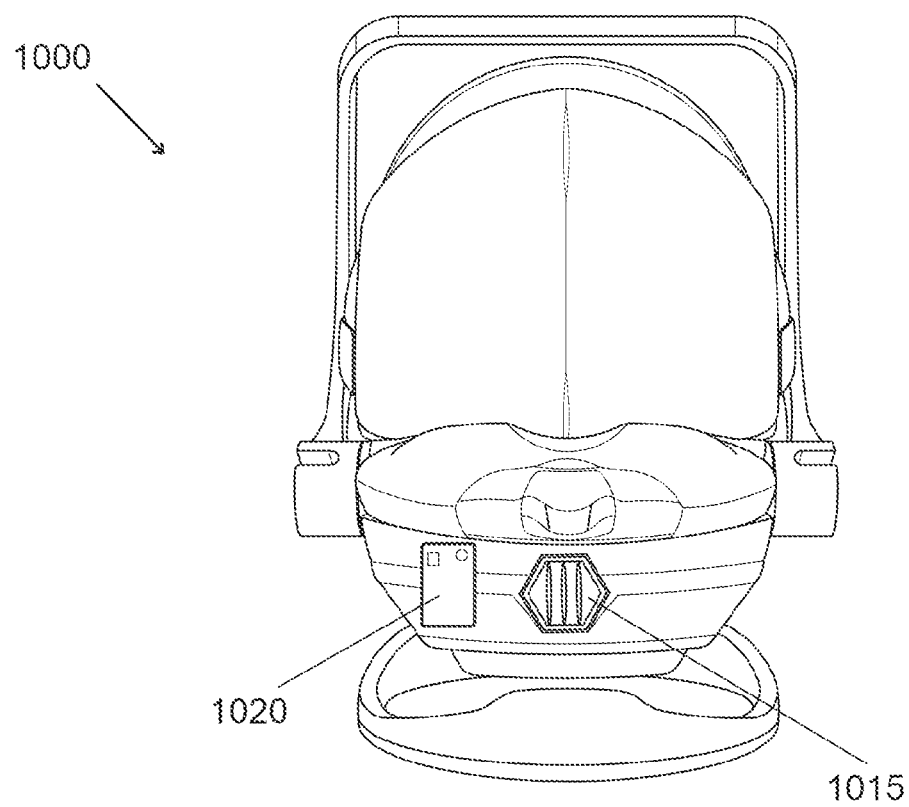
FIG. 11 illustrates an example of an infant carrier with integrated primary system devices.

As shown in FIG. 11, the infant carrier 1000 also includes an intake port 1015 and a control/display panel 1020, which function substantially as described herein with respect to the armguard embodiment.

Figure 12:
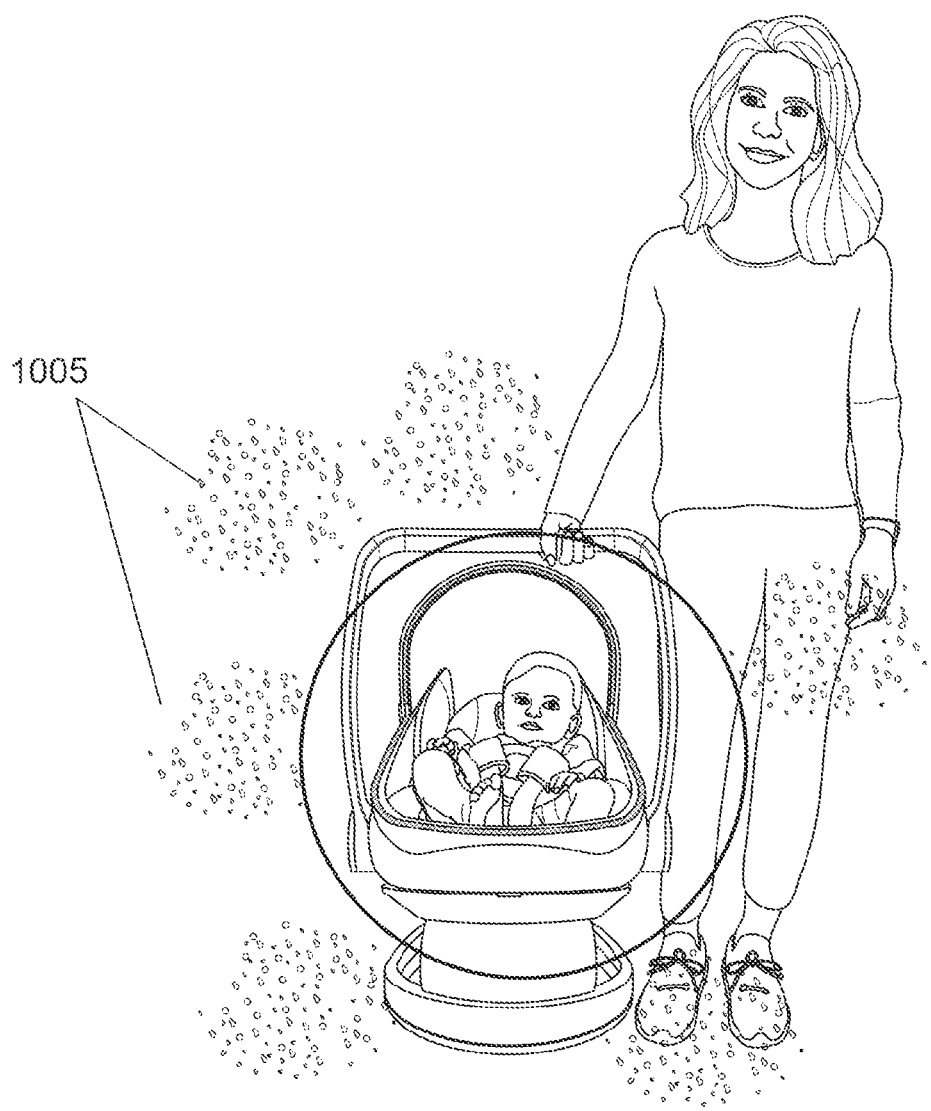
FIG. 12 illustrates a second example of an infant carrier with integrated primary system devices.
Figure 13:
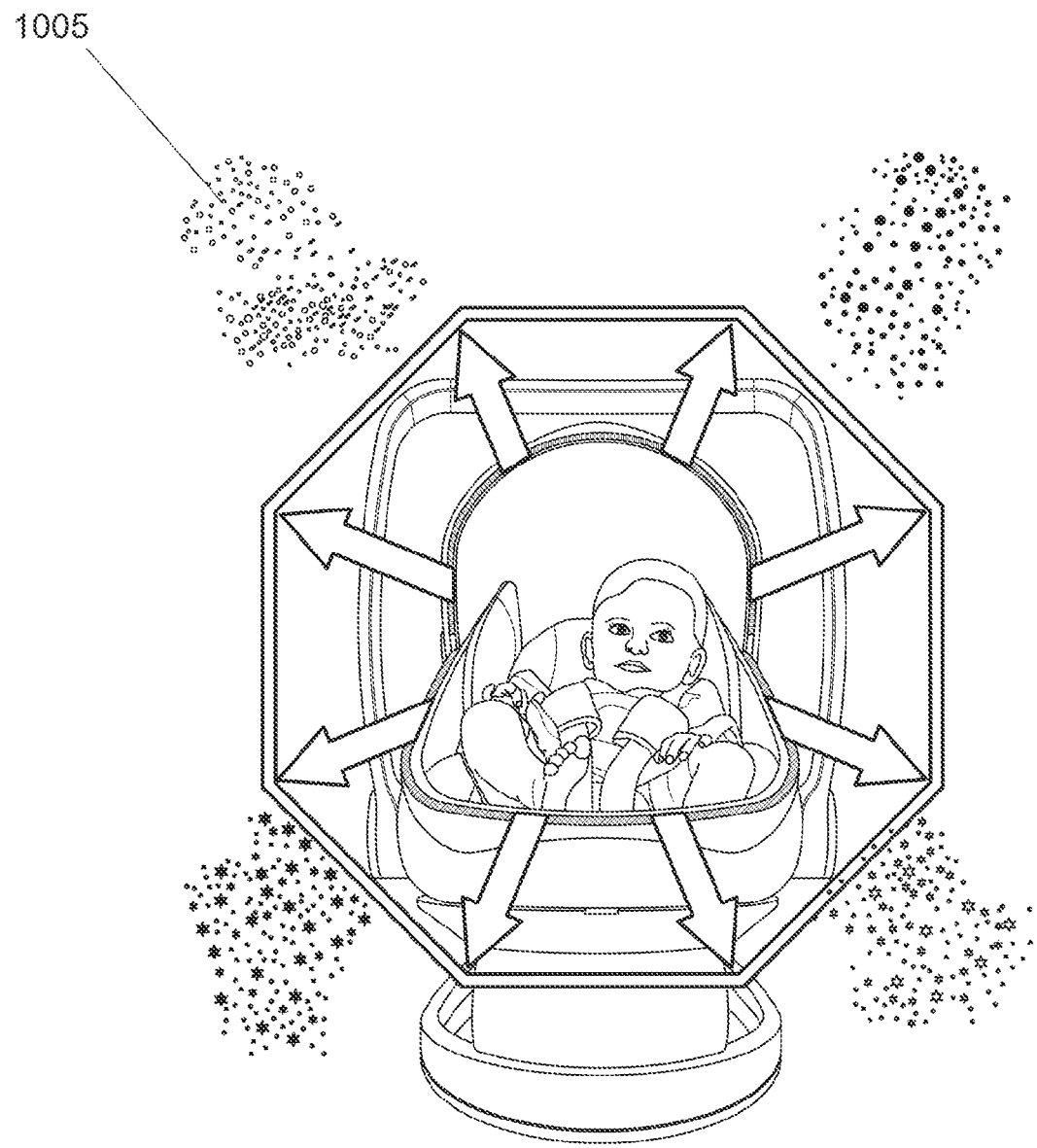
FIG. 13 illustrates a second example of an infant carrier with integrated primary system devices.

In another embodiment of an anti-pathogenic infant carrier, the anti-pathogenic devices may be placed around the carrier such that they provide 360 degrees of protection from contaminants 1005 around the infant carrier, as shown in FIGS. 12 and 13.

While an infant carrier is illustrated, the same principles may be applied to other infant containment devices, such as baby carriages, cribs, etc. Furthermore, the same principles may be applied to various animal carriers, e.g., dog and cat crates, bird cages, small animal cages, etc.

In any of these infant or animal carrier embodiments, the primary system devices may be in communication with one or more worn subsystem devices (e.g., worn by the parent or caretaker), such that when any of the subsystem devices activates, a signal is sent to the primary devices, and the primary devices activate in response to this signal. This allows the parent or caregiver to easily activate the primary devices (i.e., the devices attached to or integrate with the infant carrier) by causing their worn subsystems (e.g., on an armguard) to activate. As explained herein, the subsystems may be activated by pressing a power button or, if the subsystem is equipped with a motion detector, by quickly moving the subsystem.

Furthermore, in the embodiment where the subsystem devices are triggered by a signal from a portable device (e.g., a cellphone), the initial trigger event may cause a chain reaction of activating devices, e.g., the parent's cellphone may detect a nearby sneeze, and in response send a signal to the parent's armguard subsystem. This causes the parent's armguard to activate its anti-contaminant devices and also send a signal to the primary devices on the infant carrier, causing them to activate also.

Any of the disclosed subsystem devices may include a system setting so that users can limit power usage by disengaging or turning off the ionization function of the device and allowing the system to push contaminants away while only using the fan function.

Further, any subsystem embodiment, including eyewear, masks, face shields, armguards, gloves, may include elements for adjusting the direction and/or force of the exported mass. For example, export cylinders may be rotated (e.g., at their attachment point), and vent openings may include one or more slats that may be adjusted to control the direction of flow of the air (or other mass). To adjust the force, export cylinders may include a focusing ring, and other embodiments may include a toggle, switch, etc., to control the speed of the fan (or other expulsion means).

Another example of an anti-pathogenic primary system is a school classroom. In this embodiment, there are several primary system devices in the ceiling that are designed to extract contaminants (e.g., pathogens) up and away from the children in class. There are also several strategically angled vent openings on the floor and on the baseboards.

As the system operates, air is pushed up and over the floor from the baseboard vents and intercepts the air being pushed up from the floor vents. Because the two air masses meet at a slight upward angle, a force field blanket of protective air forms above the floor of the classroom. The air is then forced upwards, pushing dust and airborne pathogens and contaminants upwards; these contaminants are then sucked up into the vents of the ceiling.

Another example of a primary system anti-contaminant enclosure is a transportable and/or convertible tactical public safety mobile or ICS (Incident Command) headquarter vehicle such as: crime scene investigation trailers, buses, patrol vehicles, SWAT vehicles or other initial response police and/or logistical law enforcement support related vehicles.

Large scale mobile anti-contaminant ICS vehicles may also include forestry fighter trucks and rescue vehicles as well as urban fire truck and rescue ladder bucket vehicles, which may also be designated as initial response short- or long-term command-and-control or incident command headquarter vehicles.

The air quality environments within these stationary and mobile command and control enclosures are often mandated by local, state, and/or federal laws and regulatory boards or commissions such as the EPA and OSHA as well as state and county departments of health and safety established to ensure environmentally safe compliance to prevent mass population infections or contamination outbreaks.

Figure 14:
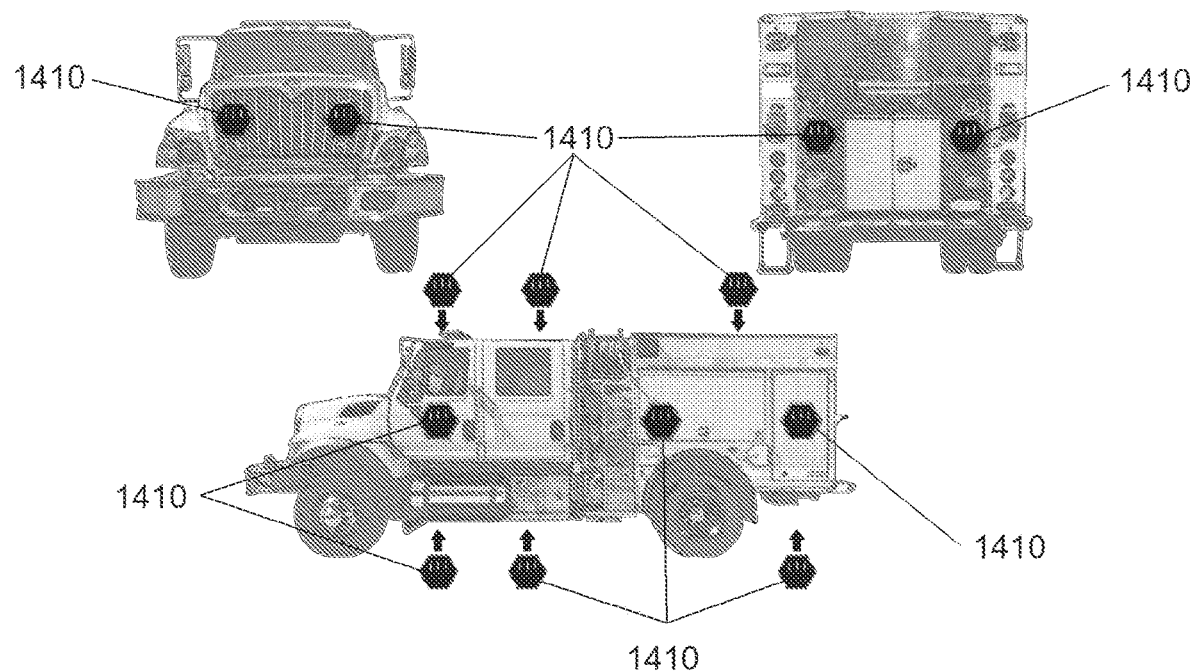
FIG. 14 illustrates an example of a firetruck with integrated primary system devices.
Figure 15:
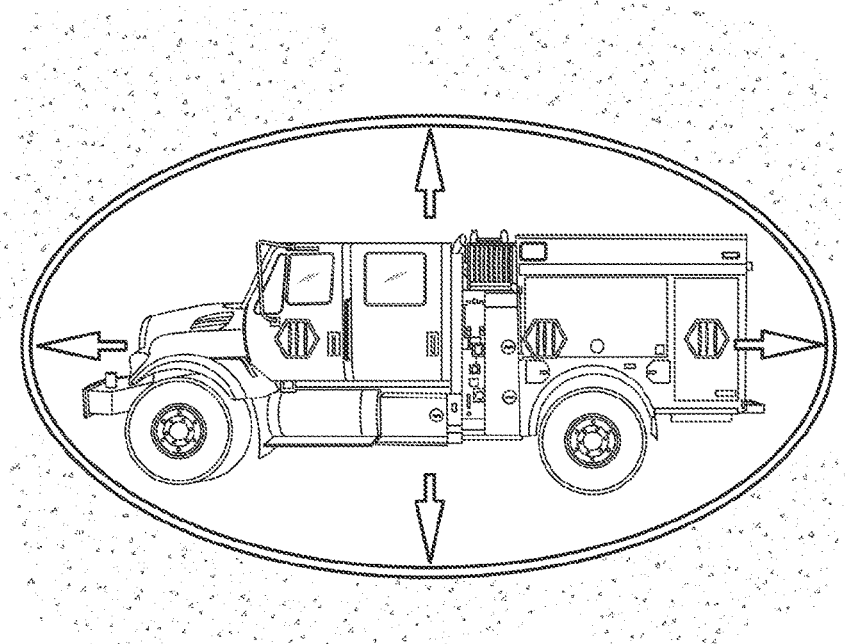
FIG. 15 illustrates an example of a firetruck with integrated primary system devices.

As shown in FIGS. 14 and 15, a firetruck for example may be outfitted with several anti-pathogenic system device vents 1410 covering the top, bottom, and side areas of the truck and able to deliver a directionally-controlled air curtain of protection of up to 360 degrees around, above, and beneath the fire vehicle. The system could be used for escaping smoke and fire danger zones in cases where the truck becomes trapped or stalled in heavy smoke or within an actual fire.

Because of the extreme nature of heavy smoke in forest fires that may overwhelm the system's filtration system, the primary air mass intake/export devices are connected to pressurized mass sources, which are self-contained within the truck. However, the functionality of the primary devices could be manual or system controlled to disengage from the self-contained mass intake source and instead use environmentally available mass in lighter smoke or fire situations. The primary system is still effective using only a fan application from the devices, by simply blowing excesses light smoke or fire away from the proximity of the fire rescue vehicle.

As a more specific example, a rescue truck may be equipped with a 360-degree anti-carcinogen air-force-field-smoke system. At maximum PSI the truck can push out air for about 8 minutes of continuous 360-degree air force field coverage. The truck may be divided into zones—e.g., a front vent export system below the front windshield, a crew cabin vent export system below the side cab windows, a top crew cabin vent export system directly over the driver cabin roof, and a rear vent export system. The user can activate each zone separately from the other zones, e.g., to blow smoke away from the engine, only the front vent export system may need to be activated, while to clear the entire front of the truck of smoke to protect the inhabitants from smoke inhalation, the front vent, crew cabin vent, and top crew cabin vent export systems my be activated. The PSI is user-controllable to allow for use in a range of conditions, e.g., light smoke, heavy smoke, etc.

This embodiment may employ wearable subsystem devices as extensions beyond the primary protective area for the purpose of preventing cross-contamination upon reentering the truck.

Figure 16:
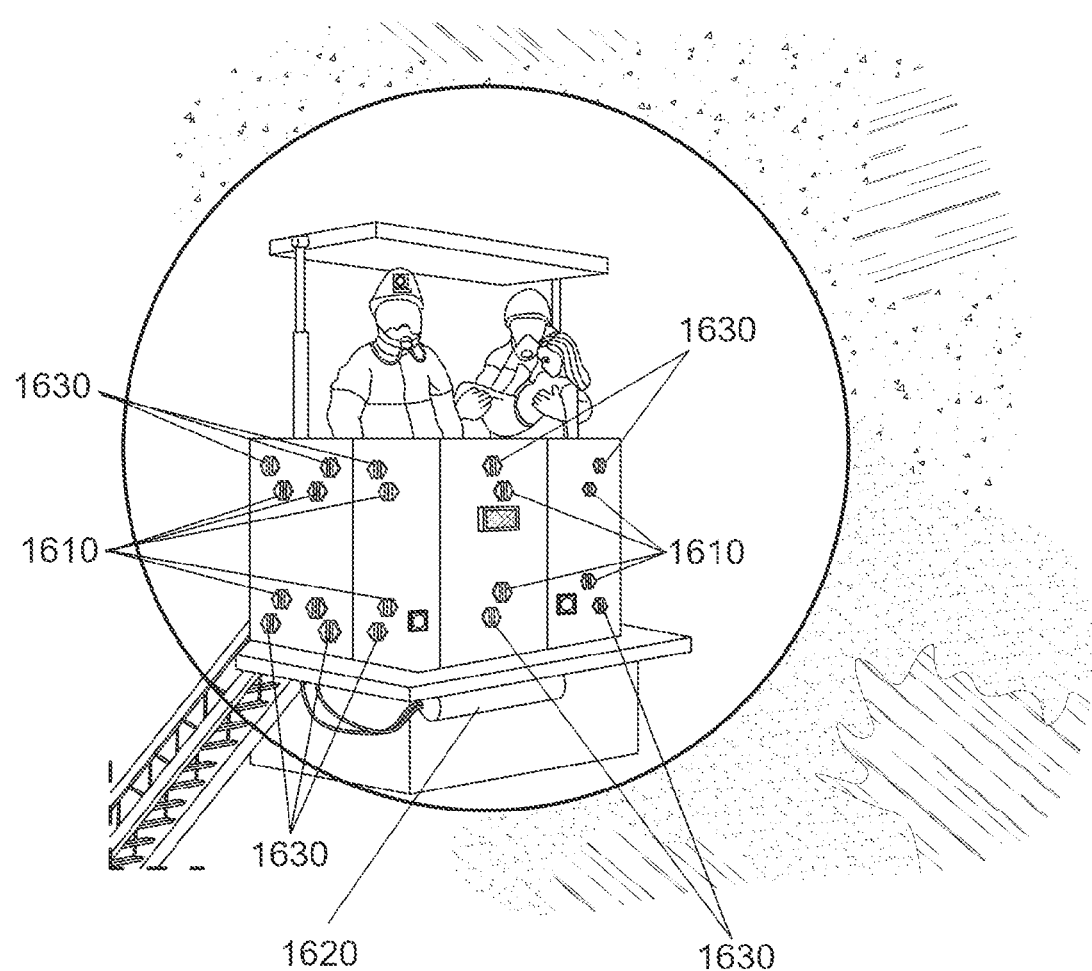
FIG. 16 illustrates an example of a fire ladder with integrated primary system devices.

Another example, illustrated in FIG. 16, is a fire truck ladder bucket equipped with a primary system. The bucket comprises a platform and overhead mount that can hold up to three people, who would be insulated within a protectively enclosed 360-degree force field of air upon activation of the primary system.

Several primary system devices 1610 are attached to and around the platform and are configured to expel smoke and fire away from the firemen inside of the bucket as it is lifted into or away from the fire and/or smoke zone. The force is supplied by a tank system 1620 under the platform.

The fire bucket system may optionally include several devices 1630 that export a controlled water supply from a hose system. The water export devices can be configured to work in conjunction with the air export devices.

PRACTICAL EMBODIMENTS

Embodiment 1—Sports and Leisure (Subsystem)

In an embodiment a Yoga instructor requires class participants to wear filtered or ionized air-force-field wristbands, instead of (or in addition to) masks, to push back or wave away lingering germs or "bad air" to prevent or reduce outbreaks such as Covid-19 and influenza while exercising or meditating in class. One student had not purchased any wristbands. However, the instructor permits him to go home and get his air-force-field chest device that is attached to his industrial work utility uniform that he wears at the power plant. He returns to class and activates the device which he then uses to push and wave away the "bad air" from around his body space.

Embodiment 2—Crowds & Sick People (Subsystem)

In an embodiment A stands in line inside a bank. A is wearing one air-force-field wristband on his left wrist and one air-force-field watch on his right wrist. B, who is two places behind A, suddenly and violently sneezes. A is aware that airborne contaminants can remain suspended in the air for several minutes and so to protect himself A immediately raises both arms and begins to wave and push the "bad air" away from his body. Because A's wristband and watch are equipped with accelerometers, the sudden movement of A's arms instantly activates both expulsion devices.

Embodiment 3—Device Syncing & General Use (Subsystem)

In a continuing embodiment, C, who is standing at the end of the line, is wearing one air-force-field forearm guard. However, C's device is not equipped with a motion detector, but it is synced with his Android phone that has a voice and sound recognition app that recognizes the sound of B's sneeze. As a result, C's forearm guard is automatically activated and so C also waves and pushes away the airborne pathogens from his body in the same manner.

Embodiment 4—Maternity & Infant Coddling (Subsystem)

In a continuing embodiment, D, who had been sitting at a desk waiting for the bank manager, is holding her newborn infant wrapped in a blanket in her arms. D had recently purchased an air-force-field armguard for infants to protect her newborn from germs because D was aware infants have weak immune systems. D is about 15 feet away when she hears B violently sneeze and so she immediately starts making circular movements around her infant's face and body to repel any airborne germs. To be extra safe D also stands up and walks towards the exit so that any lingering germs could dissipate before she returns.

Embodiment 5—Maternity Baby Strollers & Carriers (Primary System Stationary/Subsystem in Motion)

In a continuing embodiment, as D exits the bank, she holds the door open for E who is pushing her infant in a stroller. Inside E's baby stroller is a removable baby carrier. The carrier is fitted with four removable after-market anti-pathogenic infant air-force-field system devices. The devices were strategically fitted to four points around the carrier opening to protect E's newborn.

As E enters into the bank, several thousand microscopic influenza pathogens floating in the air begin to descend towards E's newborn. However, because E had activated the system, as the descending germs close in on the opening of the carrier, they are immediately deflected by the air-force-field protecting E's infant.

Embodiment 6—Maternity & Medically Prescribed Baby Strollers & Carriers (Primary System)

In a continuing embodiment, as D exits the bank, she holds the door open for E who is pushing her infant in a stroller. Inside E's baby stroller is a removable baby carrier. A factory installed anti-pathogenic Infant Force Air-Force-Field System has been installed into the opening around the carrier. The carrier has four air thrust port openings, which were strategically fitted into the carrier frame around the opening to protect E's newborn. E's particular carrier was prescribed by her pediatrician and was covered by her medical insurance because her infant was born with a lung defect.

As E enters into the bank, thousands of microscopic influenza pathogen particles floating in the air begin to descend towards E's newborn. However, because E had activated the system, as the descending germs make it close to the opening of the carrier, they are immediately deflected away by the force field of air protecting E's infant.

Embodiment 7—Work Utility Areas (Primary System & Subsystem Integration)

In a continuing embodiment, F walks up to the bank window immediately after B sneezed. However, once F arrives at the counter, F notices that air is blowing on him from several fixed positions on the counter and from the glass barrier. F realizes that the bank's primary system anti-contaminant application was activated in response to B's violent sneeze.

F also notices that all of the bank staff members behind the glass barrier are wearing anti-pathogenic devices on various parts of their bodies and that each device has a small green light which meant that they had been activated. F sees one of the bank tellers walk out from the behind the glass and step outside for a few minutes. However, the green light on the teller's anti-pathogenic chest device was not on when he left.

When the employee walks back into the bank and tries to open the door it will not open and an alarm sounds. The bank manager walks over to the teller and tells him that the primary system had alerted because he (the teller) had forgotten to turn on his device before exiting and then trying to reenter into the protective area. The manager tells the teller to go to the bathroom and decontaminate and when he returns, he (the manager) will reintegrate the teller's subsystem device with the bank's primary system enclosure so that he may safely enter back into the work area.

Embodiment 8—Law Enforcement Public Safety & Insect Bites (Subsystem)

A is a police officer who is investigating a drug overdose where B was found unconscious next to a dumpster in an ally. C is B's girlfriend and admits that she and B were shooting up heroin just before B overdosed. C also admits to officer A that she has active Tuberculosis (TB). C tells A it may be airborne but she wanted A to know because she was also once a police officer and she cares for officer A's safety.

C stands 10 feet away from officer A and starts to explain what occurred. A thanks her and presses the maximum thrust button on his new slightly tinted industrial strength anti-pathogen glasses. The glasses have two detachable air mass thrust cylinders and were funded by a federal grant and issued to all patrol officers in A's police department because of a recent spike in the number of police officers and EMS personnel in the Metro Phoenix Area who had tested positive for Covid-19 and TB.

Embodiment 9—EMT & Rescue Personnel (Subsystem)

In a continuing embodiment A noticed that the two paramedics who arrived in the ambulance were also wearing anti-pathogenic glasses when they transported B to Good Samaritan Hospital. However, unlike A's glasses, the air mass thrust cylinders were integrated into the frames of their glasses. Officer A goes to the hospital as part of his investigation and is eventually able to speak to D who is the emergency room physician who had treated B.

Embodiment 10—Hospitals & Medical Staff (Primary System & Subsystem Integration)

In a continuing embodiment A notices that doctor D is in a full biological medical suit and also has a glass shield covering his face. A also notices there are several anti-pathogen devices attached to doctor D's medical suit which cover his head, chest, legs, and back. A asks doctor D if B has died and D told him that although it was close B survived and will be admitted to a drug treatment facility.

Embodiment 11—Forest Fire Rescue and Incident Command (Primary System)

A massive forest fire has been burning in the Tonto National Forest for over two weeks. Fire jumpers team A radios to fire engine command truck B that they are behind the fire lines and trapped on the main hill by fire and smoke. Fire jumpers team A advise they are being consumed by heavy white smoke and they are having difficulties breathing and are in desperate need of oxygen. Team A tells command B they cannot last much longer and may succumb to smoke inhalation. Team A firemen also asks command B to tell their families they love them and goodbye.

The command B incident commander looks on his GPS map and asks A if they can walk 1,000 yards to the bottom of the mountain where there is a fork in the road. Fire jumpers A look through their binoculars and reply that they know where the fork in the road is but they cannot chance it because the fork is the main source of white smoke that they have been trying to avoid.

Command B tells A the fork in the road is the only way to make a rescue attempt. B also says he is sending three additional fire jumpers in fire rescue truck C. He also tells A that rescue truck C is equipped with a 360-degree Anti-Carcinogen Air-Force-Field-Smoke System. B says that according to his GPS truck C can reach them in 15 minutes. A says they are moving towards the smoke now and they should make it there in about 12-15 minutes but they will probably be unconscious or dead if rescue truck C is not on time.

Fire rescue truck C has a three-man crew. The truck captain tells his crew that at maximum PSI truck C can push out air for about 8 minutes of continuous 360-degree air force field coverage. He also tells his crew they will conserve the air pressure and will only use it if necessary because they are all out of portable oxygen (note—fire jumpers are not usually equipped with oxygen tanks).

Truck C and the rescue crew drive towards the fork in the road to rescue fire jumpers A. However, when they are about three minutes from the fork in the road a very thick wall of white smoke emerges and begins to engulf fire truck C. The captain, who is driving truck C, can't see out the front or side windows of truck C.

To compensate, the captain only turns on the front vent export system (below the front windshield), the two side crew cabin vent export systems (below the side cab windows), and the top crew cabin vent export system (directly over the driver cabin roof), which form a partial air-force-field smoke barrier around the crew cab portion of the truck C.

The captain also sets the PSI to 25% to conserve air that may be needed to rescue fire jumpers A. After the system is activated, there is more visibility and rescue truck C makes it to the rendezvous point. Truck captain C is unable to reach fire jumpers A on the radio and they are not able to see well due to the smoke. However, because some of the smoke has been displaced by the thrust of the system one crew member spots fire jumpers A who are both lying on the ground and appear to be unconscious. The two crew members exit truck C and are able to lift the two unconscious firemen aboard rescue truck C.

As rescue truck C travels back down the mountainside a very heavy cloud of white smoke begins to cover the truck. This smoke is about three times as thick as the first blanket of smoke and the GPS shows that rescue truck C is still five minutes away from command post B.

Captain C is driving and cannot see anything in front of the truck. Due to the heavy smoke, rescue truck C starts to stall and smoke begins to enter into the cab. Truck captain C radios command station B and tells them they are in extreme danger and they are now activating their 360-degree Anti-Carcinogen Air-Force-Field Smoke System at maximum thrust.

Once rescue truck C is activated at 100% PSI a 360-degree force field of air engulfs and protects the entire truck, causing the smoke to be pushed away from rescue truck C, forming a clear sphere of clean air around, on top, and beneath the truck. Rescue truck C is able to make it to the command area B and all of the fire heroes survive.

Embodiment 12—Mask (Subsystem)

A is wearing a mask to prevent or reduce his chances of contracting airborne pathogens such as Covid-19, influenza, and the common cold. A has the new style black face mask which has filtered vents and a new face shield design. There are also two detachable anti-pathogenic devices, one on each side of the mask attached proximate to the jawline.

A removes a second mask from his carry bag. The second mask is similar to the first mask, but does not have a face shield attachment. The second mask also does not have the two detachable anti-pathogenic import/export filter devices attached to the sides of the mask. Although it has the same standard filter vents as the first mask, the second mask is only equipped with a single anti-pathogenic mass import device opening under the chin portion of the jaw.

A, who has been talking with B about the recent Covid-19 epidemic, asks B which mask B wants to see. B likes A's first new mask design that A is wearing and asks him to explain how it works. A removes the mask and detaches the face shield from the breathing apparatus.

A then points to a charging port on top of each of the two import/export air mass cylinders that house the batteries and are designed to look like sleek jet engines. At the smaller end of the cylinders are openings that intake or import air mass and contaminants, while the larger ends are designed for thrusting or exporting air mass and contaminants away from a person or area. There is also a power on/off button next to a fan speed button and ionization button.

A twists the import cylinder and removes a small rechargeable battery. A then points to the cool-looking export openings which look like jet turbines. However, A explains to B that unlike a jet engine, the larger export opening is designed to thrust or emit air mass or treatments from the system and not intake air.

B points to a small button next to a blue light on the device near the power button and asks A what it is for. A tells B it is a small ionizer and that it is designed to discharge negative particles into the air that kill airborne germs and contaminants. A tells B that he upgraded his mask to have this feature and there are several methods used in the device to kill germs including a model which uses UV (Ultraviolet) light.

B points to what appears to be a small piece of dirty material inside a clear window on the housing of the device near the air mass intake opening and asks A what it is. A uses a tiny screwdriver to fully open the device. A then uses a pair of tweezers and pulls the material out and tells B that that it is a treated filter. A then replaces it with a new filter and discards the old filter.

A puts the mask back together and places it on his face but he does not reattach the face shield. A tells B that he (A) is a heart and lung surgeon and that he usually only wears the face shield when he is in the emergency room or the operating room at the hospital. He also explains that his specific system is linked to his hospital operating room primary system to ensure germs are not taken into the sterile operating room environment as physicians and medical staff enter and leave during prolonged surgeries.

B happens to be a serial smoker and rather rudely lights up a cigarette in front of A. However, A's cell phone is equipped with an accelerometer (motion detector) that is synced with A's mask device. As a physician A knows that second-hand smoke can cause cancer.

As the smoke from B's cigarette begins to move in A's direction, A shakes his cell phone two times. This activates A's anti-pathogenic mask causing the smoke to blow away from A and back towards the direction of B. A then twist the export cylinders on each device to focus a wider cone of air protection from B's cigarette.

Embodiment 13—Anti-Smoking Forearm Guard (Subsystem)

A is inside a Las Vegas casino for a weekend getaway playing various games and slot machines. Although A likes Vegas, she does not like cigarette and cigar smoke. Unfortunately for A, smoking is permitted on the casino floors. A's eyes begin to water and burn because of all of the smoke and so A decides to leave. However, before A leaves, she stops at the bar to have a drink and wait for her friends.

Once A sits down at the bar two women, B and C, sit on the left side of A and begin smoking cigarettes. A has a two-month-old infant at home. Because of the recent increase in Covid-19 cases, when A left the hospital after giving birth her insurance covered an anti-pathogenic infant forearm guard. A uses the forearm guard to shield and coddle her infant around other people, especially during flu and cold season.

A has also been using the forearm guard to cover her own face and push away the "bad air" when she is in crowded places. As the smoke from B and C's cigarettes begins to cover A, she reaches into her handbag and removes the forearm guard and places it on her left forearm.

Because A's forearm guard is equipped with a motion detector (accelerometer), A shakes her arm two times and the device activates. A then places her left elbow upright on the bar causing air from the ports to shield A by pushing the harmful smoke away from A and back towards smokers B and C.

Embodiment 14—Anti-Smoking Prescription Eyewear Use (Subsystem)

A lives in New York City and rides the train to work every day. A has bad eyes which also burn because they are sensitive to smoke and chemicals. Because of A's condition, her ophthalmologist wrote her a prescription for a pair of anti-pathogenic air-force-field glasses.

The glasses have two detachable silver light weight titanium cylinders, one on each side of the frame. Each of the cylinder housings is elongated and oval shaped and encloses a rechargeable battery. The cylinders also contain a filter, an import intake opening to receive air, a small internal ionizer, a fan system, and a mass export opening to push out a force-field of air to assist in keeping airborne germs and carcinogens away from A's eyes and respiratory tract.

While A is standing on the train, passenger B, who is standing about five feet from A, starts smoking a marijuana cigarette. A was already wearing her clear prescription glasses. She touches a small button on each cylinder which activates the system. The force of the air from her glasses pushes the smoke away and back towards marijuana smoker B. Several passengers on the train who are also wearing or carrying various styles of anti-pathogenic glasses also activate theirs to keep the smoke away from their faces.

Embodiment 15—Fashion and Leisure (Subsystem)

C is also standing on the New York subway train where B has been openly smoking a marijuana cigarette. C sees several passengers putting on their anti-pathogenic glasses to keep from breathing in carcinogens from B's marijuana cigarette. C also notices that the passengers who are wearing glasses mostly have the styles that have detachable elongated oval thrust cylinders.

Because C prefers the finer things in life, she removes a custom pair of anti-pathogenic sunglasses from her designer bag and places them on her face. C's sunglasses are also equipped with an internal ionizer to help kill germs. Unlike the glasses worn by most of the passengers, the cylinders on each side of C's glasses are not detachable and are integrated within the frame. Additionally, C's frames are gun metal gray and made with light weight titanium alloy cylinders with gold trim and are fashioned to resemble two aerodynamic jet engines.

Embodiment 16—Heat Stroke Treatment & Body Cooling (Subsystem)

A is a nurse and is inside the gym having a workout on the treadmill. After 30 minutes of running A steps off the treadmill to rest and cool off. The gym's cooling system has recently broken and the temperature inside is about 85 degrees.

A wipes the sweat off her body with a towel but she is still hot. A is wearing a new anti-pathogenic wristband on her right wrist which she received as a Christmas present. This particular model has several upgrades, including an ionizer and an air-conditioning cooling system.

A sits in a chair and turns the cooling mechanism and fan on her wristband to maximum. A then starts using it to blow cool air over her face and body. After several minutes A looks over and sees elderly woman B who has just stepped off the treadmill.

A notices B is stumbling and appears to be in distress. A walks over and asks B if she needs help. B struggles to talk and A immediately recognizes that B is suffering a stroke. The woman passes out but A catches her and gently places her on the floor and beings to render medical assistance. Several people come over to assist A and someone calls 911.

As A renders aid, general manager C asks A how he could be of assistance. A tells C that stroke victims have high core body temperatures and it was imperative to keep B's head cool. A removes her wristband and tells C to put it on and keep it held over B's head. C does what he was asked until paramedics arrived and transport B to the hospital. Fortunately, B survives.

Embodiment 17—Health and Wellness (Subsystem)

Nurse A also uses her anti-pathogenic wristbands as a body cooling system when she exercises.

Embodiment 18—Medical Application (Subsystem)

Nurse A is also a 60-year-old menopausal woman who often uses her gym anti-pathogenic wristband to cool herself during hot flashes.

Embodiment 19—Fire Ladder & Bucket Rescue (Primary System & Subsystem Integration)

Philadelphia fire truck ladder A is dispatched to a fire at 1776 Philadelphia Street because of a report of a building fire in an apartment complex. Truck A is advised that a ladder bucket will also be needed to rescue a ten-year-old little girl who is trapped in her apartment on the twelfth floor of the building. When ladder A arrives, B is crying for help from her apartment window.

All of the lower-level floors are fully engulfed with flames and thick black smoke that is now covering up a large section of the building and most of B who has been leaning out of the window and is choking and gasping for air. If B is not rescued within 5 minutes, she will likely succumb to the smoke and fire.

Fortunately, Philadelphia fire truck ladder A is the first truck on the east coast to be equipped with the new 360-degree Anti-Carcinogen Air-Force-Field Ladder Bucket System. The bucket opens up into a 6×6 platform and overhead mount that can hold two firemen and three people who may be insulated within a protectively enclosed 360-degree force field of air and/or water.

Two firemen are lifted up to the sixth floor. However, as they near the window to extract the girl B, large plumes of black smoke drift out of B's window and upwards from the apartment windows directly below B's apartment, totally engulfing the firemen, making it impossible to see anything. One of the firemen activates the system, which then creates a massive air bubble clearing around the ladder and the heroes are able to safely rescue the trapped little girl B.

Embodiment 20—Evacuation of Contaminants from Structures (Primary System)

A class of Kindergarten children are in the school district's first of its kind anti-pathogenic 30×20 classroom. There are several vents in the ceiling that are designed to extract germs up and away from the children in class. There are also several strategically angled vent openings on the floor and baseboards. Each vent is connected to a primary system export device.

Air that is pushed up and over the floor from the baseboard vents intercepts the air pushed up from the floor vents. Because the two air masses meet at a slight upward angle, a force field blanket of protective air forms above the floor of the classroom. The air is then forced upwards, pushing up dust, airborne pathogens, and contaminants. These contaminants are then sucked up into the vents of the ceiling.

Teacher A is writing the alphabet on the board in class when mother B knocks on the door. Teacher A opens the door and notices that mother B has brought her son C to school because C had missed the bus this morning. Teacher A thanks mother B for bringing her son C to class after which mother A leaves.

Teacher A tells B to take his usual seat at the table with the other children because they are learning their alphabets today. As B walks up to the table he suddenly stops and sneezes. However, before airborne pathogens from B's cold virus could reach the table to contaminate the other children, the vents on the floor and baseboards of the room diffuse and push the airborne germs up towards the ceiling where they are then sucked up into the filtered ceiling vents Embodiment 21—Anti-Pathogenic Air-Force-Field Insect Protection (Subsystem)

A is a police officer who works in Florida where there are a lot of mosquitos, gnats, and other insects. In the last few weeks, the number of mosquitos in Tallahassee has dramatically increased and several dozen community members have contracted the West Nile Virus and Malaria because of the recent rains and dirty settling water which is causing the mosquitos to lay more eggs.

Fortunately for A, his department recently issued him a pair of anti-pathogenic glasses due to the recent spike in Covid-19 and Tuberculosis cases in the county, which A and his squad mates have also been using on calls to blow away the pesky disease carrying insects from their faces and bodies.

Embodiment 22—Anti-Pathogenic Attachment for a Fireman's Face Mask (Subsystem)

Fireman A is about to enter a burning, smoke-filled home. A checks the breathing apparatus attached to his face and eye mask shield system.

On each side of A's face mask are two (4 total) high powered industrial strength anti-pathogenic devices used to export air mass away from A's face at extremely high pressures. The air mass intake port systems of the devices are self-contained and sourced from an independent tank system on A's back.

A hears a whimpering dog inside the house and immediately runs into the home. A believes the sound is coming from the living room. However, A is partially blinded by the thick black smoke. A turns up his anti-pathogenic mask system to high power, causing a very powerful force field of air to form in front of and around A's face and head, allowing A to see. A is then able to locate the dog sitting in a cage in the living room. A rescues the dog and is able to safely return it to its owner.

Embodiment 23—Anti-Smoking Gloves (Subsystem)

A is standing on the New York subway train where B has been openly smoking cigarettes. A sees several passengers putting on their anti-pathogenic glasses to keep from breathing in smoke from B's cigarette. A also notices most passengers have glasses that only have detachable import/export cylinders.

A does not have a pair of anti-pathogenic glasses. However, A is wearing a pair of anti-pathogenic gloves which she purchased for overseas travel, where smoking in business and restaurants are often permitted.

Each of A's gloves is equipped with a lightweight bracelet-like fitting that rotates around the circumference of A's wrist. Each wristband has an enclosure snap-in anchor design that receives a jet engine-shaped anti-pathogenic import/export device. The anchors are rotatable with the bracelet fittings around the top (i.e., over the back of the hand), sides, and bottom of the wrist.

A's gloves are also vented with a hollow hard material surface. The surface contours and follows the outside shape of A's palms and allows the rotatable devices to align with a hollow plastic opening under A's palm so that air mass which is imported and/or exported from the device is channeled under the palms and out through the palm vents. This allows A to open her hand(s) wide and expel air-mass from the palm area of her hands causing filtered air mass to push smoke and irritants away from her eyes and respiratory system.

A's anti-pathogenic glove device also has a system setting so that A can save her battery or charging system by disengaging or turning off the air filtration and/or ionization function of the device, and allowing the system to push smoke away while only using a fan function.

In the continuing embodiment, as smoke from B's cigarette travels across the cab towards A, she presses a button on the system which turns off the filter and ionizer. A then holds out both of her palms causing air mass from her gloves to fan away the smoke and push it back in the direction of B.

Embodiments of the subject matter and the functional operations described in this specification can be implemented in one or more of the following: digital electronic circuitry; tangibly-embodied computer software or firmware; computer hardware; and combinations thereof. Such embodiments can be implemented as one or more modules of computer program instructions encoded on a non-transitory medium for execution by a data processing apparatus.

As used herein, the term "data processing apparatus" comprises all kinds of apparatuses, devices, and machines for processing data, including but not limited to, a programmable processor, a computer, and/or multiple processors or computers. Exemplary apparatuses may include special purpose logic circuitry, such as a field programmable gate array ("FPGA") and/or an application specific integrated circuit ("ASIC"). In addition to hardware, exemplary apparatuses may comprise code that creates an execution environment for the computer program (e.g., code that constitutes one or more of: processor firmware, a protocol stack, a database management system, an operating system, and a combination thereof).

The term "computer program" may also be referred to or described herein as a "program," "software," a "software application," a "module," a "software module," a "script," or simply as "code." A computer program may be written in any programming language, and it can be deployed in any form, including as a standalone program or as a module, component, subroutine, or other unit suitable for use in a computing environment. A computer program can be deployed and/or executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as but not limited to an FPGA and/or an ASIC.

Computers suitable for the execution of the one or more computer programs include, but are not limited to, general purpose microprocessors, special purpose microprocessors, and/or any other kind of central processing unit ("CPU").

Computer readable media suitable for storing computer program instructions and data include all forms of nonvolatile memory, media, and memory devices. For example, computer readable media may include one or more of the following: semiconductor memory devices, such as ROM or RAM; flash memory devices; magnetic disks; magneto optical disks; and/or CD-ROM and DVD-ROM disks. The processor and the memory can be supplemented by, or incorporated in, special purpose logic circuitry.

To provide for interaction with a user, embodiments may be implemented on a computer having any type of display device. Exemplary display devices include, but are not limited to one or more of: projectors, cathode ray tube ("CRT") monitors, liquid crystal displays ("LCD"), light-emitting diode ("LED") monitors, and/or organic light-emitting diode ("OLED") monitors. The computer may further comprise one or more input devices by which the user can provide input to the computer. Input devices may comprise one or more of: keyboards, pointing devices (e.g., mice, trackballs, etc.), and/or touch screens. Moreover, feedback may be provided to the user via any form of sensory feedback (e.g., visual feedback, auditory feedback, or tactile feedback). A computer can interact with a user by sending documents to and receiving documents from a device that is used by the user.

Embodiments of the subject matter described in this specification can be implemented in a computing system that includes one or more of the following components: a back-end component (e.g., a data server); a middleware component (e.g., an application server); a frontend component (e.g., a client computer having a graphical user interface ("GUI") and/or a web browser through which a user can interact with an implementation of the subject matter described in this specification); and/or combinations thereof. The components of the system can be interconnected by any form or medium of digital data communication.

The computing system may include clients and/or servers. The client and server may be remote from each other and interact through a communication network. The relationship of client and server arises by virtue of computer programs running on the respective computers and having a client-server relationship to each other.

Various embodiments are described in this specification, with reference to the detailed discussed above, the accompanying drawings, and the claims. Numerous specific details are described to provide a thorough understanding of various embodiments. However, in certain instances, well-known or conventional details are not described in order to provide a concise discussion. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the embodiments.

The embodiments described and claimed herein and drawings are illustrative and are not to be construed as limiting the embodiments. The subject matter of this specification is not to be limited in scope by the specific examples, as these examples are intended as illustrations of several aspects of the embodiments. Any equivalent examples are intended to be within the scope of the specification. Indeed, various modifications of the disclosed embodiments in addition to those shown and described herein will become apparent to those of ordinary skill in the art, and such modifications are also intended to fall within the scope of the appended claims. Furthermore, any reference to singular includes plural embodiments, and any reference to more than one component may include a singular embodiment.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple products.

All references including patents, patent applications and publications cited herein are incorporated herein by reference in their entirety and for all purposes to the same extent as if each individual publication or patent or patent application was specifically and individually indicated to be incorporated by reference in its entirety for all purposes.

What is claimed is:

1. A system for keeping a protected area substantially clean from contaminants dangerous to a living organism, the system comprising:
one or more primary mass expulsion devices proximate to a periphery of the protected area, each primary mass expulsion device configured to export mass away from the protected area at a force calculated to prevent encroachment of contaminants into the protected area, each primary mass expulsion device comprising a communication module; and
one or more subsystem devices each comprising a portable mass expulsion device configured to be worn on a user's body, each portable mass expulsion device comprising a mass expulsion means, a power source, a mass export port, a mass intake port, and a communication module;
wherein through operation of the communication modules of the one or more primary mass expulsion devices and the communication modules of the one or more subsystem devices, the one or more primary mass expulsion devices communicate with the one or more subsystem devices.

2. The system of claim 1, wherein the one or more primary mass expulsion devices are disposed on a mobile system platform, and wherein the system is configured to protect one to a plurality of organisms within a defined vicinity or confines of the mobile system platform.

3. The system of claim 2, wherein the one or more primary mass expulsion devices are affixed to or integrated with a means for containing infants, wherein the means for containing infants comprises at least one opening for retrieving a contained infant, wherein the one or more primary mass expulsion devices are affixed to or integrated with the means for containing infants proximate a periphery of the opening for retrieving a contained infant, wherein the one or more primary mass expulsion devices are configured to export a mass of protection thereby repulsing or diffusing airborne contaminants descending upon or projected towards the contained infant.

4. The system of claim 3, wherein the one or more primary mass expulsion devices are configured to provide 360 degrees of protection around the infant containing means.

5. The system of claim 2, wherein at least one subsystem device of the one or more subsystem devices is configured to alert at least one primary mass expulsion device of the one or more primary mass expulsion devices when the at least one subsystem device activates, and the alerted primary mass expulsion devices are configured to respond to a subsystem alert by activating.

6. The system of claim 2, wherein the one or more primary mass expulsion devices are affixed to or integrated with a means for containing animals, wherein the means for containing animals comprises at least one opening for retrieving a contained animal, wherein the one or more primary mass expulsion devices are affixed to or integrated with the means for containing animals proximity a periphery of the opening for retrieving a contained animal, wherein the one or more primary mass expulsion devices are configured to export a mass of protection thereby repulsing or diffusing airborne contaminants descending upon or projected towards the contained animal.

7. The system of claim 6, wherein the one or more primary mass expulsion devices are configured to provide 360 degrees of protection around the animal containing means.

8. The system of claim 2, wherein the one or more primary mass expulsion devices are integrated with or attached to a transport vehicle having at least one wheel attachment facilitated by an engine or alternative fuel function.

9. The system of claim 2, wherein the one or more primary mass expulsion devices are integrated with or attached to a transport vehicle having at least one wheel attachment facilitated by power of a living creature.

10. The system of claim 2, wherein the one or more primary mass expulsion devices are integrated with or attached to a transport vehicle, and wherein the transport vehicle comprises an emergency services vehicle.

11. The system of claim 2, wherein the one or more primary mass expulsion devices are integrated with or attached to a transport vehicle, and wherein the transport vehicle comprises a public safety vehicle.

12. The system of claim 2, wherein the one or more primary mass expulsion devices are integrated with or attached to a mechanical lifting system, and wherein the mechanical lifting system is attached to an emergency services vehicle.

13. The system of claim 2, wherein the one or more primary mass expulsion devices are integrated with or attached to a fire ladder bucket platform designed for lifting personnel into or proximate of a hazard zone, wherein the one or more primary mass expulsion devices are configured to expel mass matter at least one direction away from a base, wall, or ceiling of the bucket platform.

14. The system of claim 13, wherein at least one primary mass expulsion device of the one or more primary mass expulsion devices exports air mass.

15. The system of claim 13, wherein at least one primary mass expulsion device of the one or more primary mass expulsion devices exports liquid mass.

16. The system of claim 1, wherein the contaminants comprise one or more of the following: pathogens, spores, chemicals, smoke, steam, aerosols, insects, and fire.

17. The system of claim 1, wherein the one or more primary mass expulsion devices are configured to operate intermittently.

18. The system of claim 1, wherein the one or more primary mass expulsion devices are configured to synchronously start operation in response to detection of motion within the protected area.

19. The system of claim 1, wherein the one or more primary mass expulsion devices intake mass and the intake mass is filtered.

20. The system of claim 1, wherein the one or more primary mass expulsion devices intake mass from an independently contained source of mass.

21. The system of claim 1, wherein the one or more primary mass expulsion devices and the one or more subsystem devices are configured to operate when not in communication with each other.

22. The system of claim 1, wherein each subsystem device comprises one or more of the following: eyewear, face masks, face shields, hats, helmets, wristbands, gloves, mittens, watches, arm guards, forearm guards, leg guards, shin guards, knee guards, neck fans, necklaces, vests, face mask vents, face shield vents, and respiratory mouth shields.

23. The system of claim 1, wherein one or more of the one or more subsystem devices are attached to a piece of clothing.

24. The system of claim 1, wherein one or more of the one or more subsystem devices are configured to hang around the body of a user.

25. The system of claim 1, wherein at least one portable mass expulsion device of the one or more subsystem devices intakes mass from a portable and independently contained source of mass.

26. The system of claim 1, wherein at least one portable mass expulsion device of the one or more subsystem devices further comprises a protective covering over the mass intake port to shield internal components of the portable mass expulsion device from damage.

27. The system of claim 1, wherein one or more of the one or more subsystem devices is are activated by a motion detection means contained within or in communication with the one or more of the one or more subsystem devices.

28. The system of claim 27, wherein the motion detection means comprises an accelerometer contained within a portable communication device, and wherein the portable communication device is in communication with the subsystem device.

29. The system of claim 1, wherein one or more of the one or more subsystem devices comprises an eyewear protective accessory, wherein at least one portable mass expulsion device is affixed to or integrated with the eyewear protective accessory.

30. The system of claim 1, wherein one or more portable mass expulsion is devices are rotatably affixed to one or more of the one or more subsystem devices, such that the direction of the mass exported from the rotatably affixed portable mass expulsion devices is user-adjustable.

31. The system of claim 1, wherein one or more portable mass expulsion device further comprises a means for adjusting the force of the mass export.

32. The system of claim 1, wherein one or more of the one or more subsystem devices comprises an ion emitter configured to emit charged ions.

33. The system of claim 1, wherein one or more of the one or more subsystem devices comprises a mask, wherein at least one portable mass expulsion device is affixed to or integrated with the mask.

34. The system of claim 1, wherein one or more of the one or more subsystem devices sends an alert when one or more of its portable mass expulsion devices is turned off after breaching a defined proximity outside of the protected area of the system to signal a decontamination notification.

35. The system of claim 1, wherein one or more of the one or more subsystem devices sends an alert when one or more of its portable mass expulsion devices is turned off prior to breaching a defined proximity within the protected area of the system to signal a decontamination notification.

36. The system of claim 1, wherein one or more of the one or more subsystem devices sends an alert when one or more of its portable mass expulsion devices activates to signal a decontamination notification.

37. The system of claim 1, wherein one or more of the one or more subsystem devices comprises an armguard configured to fit over a forearm of a user.

38. The system of claim 1, wherein at least one subsystem device of the one or more subsystem devices comprises a human head covering, wherein the head covering covers at least one area above the top of a wearer's neck line, wherein the at least one subsystem device is configured to export mass away from at least one surface area of the wearer's head.

39. The system of claim 1, wherein at least one subsystem device of the one or more subsystem devices comprises a mask, the mask comprising one or more mask export vents integral with or affixed to a surface of the mask, the mask comprises one or more matter export means, the matter export means configured to force mass matter sideways over at least one cross-sectional surface area of the mask, thereby forming a vertical or horizontal mass force-field barrier above the surface of the mask to limit or prevent airborne contaminants from contacting or adhering to a mask surface material.

40. The system of claim 1, wherein at least one subsystem device of the one or more subsystem devices comprises a hand covering, wherein the covering is designed or structured to cover at least one portion of a hand of a user forward of the user's wrist.

41. The system of claim 1, wherein the protected area is a medical research facility.

42. The system of claim 1, wherein the protected area is a tactical command center.

43. The system of claim 1, wherein the protected area is a factory operational area.

44. The system of claim 1, wherein the protected area is a power plant operational area.

45. The system of claim 1, wherein the protected area is a learning center.

46. The system of claim 1, wherein the protected area is an office center.

47. The system of claim 1, wherein the protected area is a transaction area.

48. The system of claim 1, wherein the protected area is a medical treatment facility.

49. The system of claim 1, wherein the protected area is a health and wellness center.

\* \* \* \* \*